US006472201B1

(12) United States Patent
Bochner et al.

(10) Patent No.: US 6,472,201 B1
(45) Date of Patent: *Oct. 29, 2002

(54) COMPARATIVE PHENOTYPE ANALYSIS

(75) Inventors: Barry Bochner, Alameda, CA (US); Eugenia Panomitros, San Francisco, CA (US)

(73) Assignee: Biolog, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/752,168

(22) Filed: Dec. 29, 2000

Related U.S. Application Data

(63) Continuation of application No. 09/574,087, filed on May 18, 2000, which is a continuation of application No. 09/333,802, filed on Jun. 15, 1999, now abandoned, which is a continuation-in-part of application No. 09/098,066, filed on Jun. 16, 1998, now Pat. No. 6,046,021, which is a continuation-in-part of application No. 08/762,656, filed on Dec. 9, 1996, now Pat. No. 5,882,882, which is a continuation-in-part of application No. 08/421,377, filed on Apr. 12, 1995, now Pat. No. 5,627,045.

(51) Int. Cl.[7] ............................ C12M 1/34; C12M 3/00; C12N 1/04; C12N 1/00
(52) U.S. Cl. ........................ 435/288.4; 435/4; 435/29; 435/32; 435/34; 435/7.31; 435/7.32; 435/822; 435/911
(58) Field of Search ...................... 435/4, 29, 34, 435/32, 7.31, 7.32, 822, 911, 288.4

(56) References Cited

U.S. PATENT DOCUMENTS

| | | |
|---|---|---|
| 3,107,204 A | 10/1963 | Brown et al. |
| 3,197,384 A | 7/1965 | Goldman |
| 3,935,067 A | 1/1976 | Thayer |
| 4,076,592 A | 2/1978 | Bradley |
| 4,129,483 A | 12/1978 | Bochner |
| 4,235,964 A | 11/1980 | Bochner |
| 4,241,186 A | 12/1980 | Roth |
| 4,282,317 A | 8/1981 | Roth |
| 4,326,052 A | 4/1982 | Kang et al. |
| 4,326,053 A | 4/1982 | Kang et al. |
| 4,343,782 A | 8/1982 | Shapiro |
| 4,448,534 A | * 5/1984 | Wertz et al. |
| 4,603,108 A | 7/1986 | Bascomb |
| 5,063,090 A | 11/1991 | Wannlund |
| 5,134,063 A | 7/1992 | Bochner |

(List continued on next page.)

FOREIGN PATENT DOCUMENTS

| | | |
|---|---|---|
| EP | 0 329 120 | 8/1989 |
| EP | 0 451 775 | 10/1991 |
| WO | WO 82/02563 | 8/1982 |
| WO | WO 94/01528 | 1/1994 |
| WO | WO 94/19698 | 9/1994 |

OTHER PUBLICATIONS

Stager et al. Clin. Microbiol. Rev. 1992. vol. 5, No. 3, pp. 302–325.*

(List continued on next page.)

*Primary Examiner*—Christopher R. Tate
(74) *Attorney, Agent, or Firm*—Medlen & Carroll, LLP

(57) ABSTRACT

The present invention relates to growing and testing microorganisms in a multitest format which utilizes a gel forming matrix for the rapid screening of clinical and environmental cultures. The present invention is suited for the characterization of commonly encountered microorganisms (e.g., *E. coli, S. aureus,* etc.), as well as commercially and industrially important organisms from various and diverse environments (e.g., the present invention is particularly suited for the growth and characterization of the actinomycetes and fungi). The present invention is also particularly suited for comparative analysis of phenotypic differences between cell types, including strains of microorganisms that have been designated as the same genus and species, as well as other cell types (e.g., mammalian, insect, and plant cells).

24 Claims, 2 Drawing Sheets

U.S. PATENT DOCUMENTS

| | | |
|---|---|---|
| 5,164,301 A | 11/1992 | Thompson et al. |
| 5,188,965 A | 2/1993 | Wannlund |
| 5,223,402 A | 6/1993 | Abbas et al. |
| 5,340,747 A | 8/1994 | Eden |
| 5,501,959 A | 3/1996 | Lancaster et al. |
| 5,589,350 A | 12/1996 | Bochner |
| 5,627,045 A | 5/1997 | Bochner et al. |
| 5,800,785 A | 9/1998 | Bochner |
| 5,843,699 A | 12/1998 | Strenkoski et al. |
| 5,882,882 A | 3/1999 | Bochner et al. |
| 5,888,760 A | 3/1999 | Godsey et al. |
| 5,888,825 A | 3/1999 | Carr et al. |

OTHER PUBLICATIONS

Fernandez et al. Letters Appl. Microbiol. 1993. vol. 17, No. 6, pp 292–296, BIOSIS abstract enclosed.*

Klingler et al. Appl. Environ. Microbiol. 1992. vol. 58, No. 6, pp. 2089–2092, BIOSIS abstract enclosed.*

American Public Health Association, *Standard Methods for the Examination of Water and Wastewater*, 16th ed., APHA, Washington, D.C., pp. 864–866 (1985).

Atlas in *Handbook of Microbiological Media*, CRC Press, Boca Raton, FL, p. 834 (1993).

Williams, editor of vol. 4; John G. Holt, editor in chief, *Bergey's Manual® of Systematic Bacteriology*, Williams & Wilkins, pp. 2334–2338 (1989).

Black, *Microbiology: Principles and Applications*, 2nd., Prentice Hall, Englewood Cliffs, NJ, p. 153 (1993).

Bochner, "Sleuthing out Bacterial Identities," *Nature* 339:157–158 (1989).

Bochner, "Breathprints' at the microbial Level," *ASM News* 55:536–539 (1990).

Bochner and Savageau, "Generalized Indicator Plate for Genetic, Metabolic, and Taxonomic Studies with Microorganisms," *Appl. Environ. Microbiol.,* 33:434–444 (1977).

Braithwaite and Smith, in "Chromatographic Methods," Chapman et al. (eds.), pp 24–50, London (1985).

Cross, "Growth and Examination of Actinomycetes–Some Guidelines," *Bergey's Manual® of Determinative Bacteriology*, 9th ed., Holt et al. (eds.), Williams & Wilkins, Baltimore, pp. 605–609 (1994).

DeRisi et al., "Exploring the Metabolic and Genetic Control fo Gene Expression on a Genomic Scale," *Science* 278: 680–686 (1997).

Glaser, "Functional Genomics Shifts Drug Discovery Paradigm to Protein Expression & Separation," *Genet. Engin. News*, pp. 1, 6 and 15 (Sep. 15, 1997).

Goffeau et al., "Life with 6000 Genes," *Science* 274: 546–567 (1996).

Graan, et al., "Methyl Purple, an Exceptionally Sensitive Monitor of Chloroplast Photosystem I Turnover: Physical Properties and Synthesis," *Anal Biochem.*, 144:193–198 (1985).

Hindler (ed.), "Antimicrobial Susceptibility Testing," in *Clinical Microbiology Procedures Handbook*, Isenberg (ed.), American Society for Microbiology, pp. 5.0.1 through 5.25.1 (1994).

Kobayashi, "Actinomycetes: The fungus–like bacteria," in *Microbiology*, 4th ed., Davis et al. (eds.), J.B. Lippincott Co., New York, pp. 665–671 (1990).

Koch, "Methods for the Study of Pathogenic Organisms," in *Milestones in Microbiology*, Brock (ed.), American Society for Microbiology, pp. 101–108 (1961).

Land et al., "Aerobic pathogenic Actinomycetales," in *Manual of Clinical Microbiology*, Balows et al. (eds.), pp. 340–359 (1991).

Land, "Mycology," in *Clinical Microbiology Procedures Handbook*, Land et al. (eds.), American Society for Microbiology, pp. 6.10.1 through 6.10.5 (1994).

Pennisi, "Laboratory Workhorse Decoded," *Science* 277: 1432–1434 (1997).

Reasoner and Geldreich, "A New Medium for the Enumeration and Subculture of Bacteria from Potable Water," *Appl. Environ. Microbiol.*, 49:1–7 (1985).

Shirling and Gottlieb, in "Methods for Characterization of *Streptomyces*Species" *Int'l J. System. Bacteriol.*, 16:313–330 (1966).

Smith et al., "Functional Analysis of the Genes of Yeast Chronosome V by Genetic Footprinting," *Science* 274:2069–2074 (1997).

Rieger et al., "Large–Scale Phenotypic Analysis—the Pilot Project on Yeast Chromosome III," *Yeast* 13:1547–1562 (1997).

Oliver et al., "Systematic functional analysis of the yeast genome," *Tib–Tech*16:373–378 (1998).

Hampsey, "A Review of Phenotypes in *Saccharomyces cerevisiae,*" *Yeast*13:1099–1133 (1997).

Seiler and Busse, "Identification of Yeasts with Microtiter Plates," *Forum Mikrobiologie* 11:505–509 (1988).

Heard and Fleet, "A Convenient Microtitre tray Procedure for Yeast Identification," *J. Appl. Bacterial.*, 68:447–451 (1990).

Shelef et al., "Novel selective and non–selective optical detection of microorganisms," *Lett. Appl. Microbiol.*, 25: 202–206 (1997).

Abbott et al., "*Escherichia coli* O157:H7 Generates a Unique Biochemical Profile on MicroScan Conventional Gram–Negative Identification Panels," *J. Clin. Microbiol.*, 32: 823–824 (1994).

Coudron et al., "Tetrazolium Reduction as an Aid for Streptococcal Growth Detection with Agar Dilution Susceptibility Testing," *J. Clin. Microbiol.*, 18:765–769 (1983).

Bartlett and Mazens, "Rapid Antimicrobial Susceptibility Test Using Tetrazolium Reduction," *Antimicrob. Agents Chemother.* 15:769–774 (1979).

Kouda et al., "Bioluminescent Assay as a Potential Method of Rapid Susceptibility Testing," *Microbiol. Immunol.*, 29:309–315 (1985).

Urban and Jarstrand, "Rapid determination of the susceptibility of bacteria to antibiotics with 'Sensititre' plates and nitroblue tetrazolium," *J. Antimicrob. Chemother*, 8:363–369 (1981).

Kroemer et al., "Mikrotitrierverfahren zur Bestimmung der Antibiotischen Empfindlichkeit bei Staphylokokken mit Tetrazoliumsalzen," ("Use of a Microtiter–System for the Determination of the antibiotic Susceptibility of a Staphylococci with Tetrazolium Salts," *Zbl. Bakt. Hyg.*, I. Abt. Orig., A 239: 42–45 (1977).

Miller et al., "Evaluation of Biolog for identification of Members of the Family Micrococcaceae," *J. Clin. Microbiol.*, 31(12): 3170–3173 (1993).

Miller et al., "Evaluation of API An–Ident and RapId ANA II Systems for Identification of Actinomyces Species from Clinical Specimens," *J. Clin. Microbiol.*, 33(2):329–330 (1995).

Kampfer et al., "A numerical classification of the genera Streptomyces and Streptoverticillium using miniaturized physiological test," *J. Gen. Microbiol.*, 137:1831–1891 (1991).

Kampfer and Kroppenstedt, "Probabilistic Identification of Streptomycetes Using Miniaturized Physiological Tests," *J. Gen. Microbiol.*, 137:1893–1902 (1991).

Seiler and Busse, "The Yeasts of Cheese Brines," *Intern. J. Food Microbiol.*, 11:289–304 (1990).

Seiler et al., "Identification of Moulds With Microtitration Plates," *Milchwissenschaft* 49:248–252 (1994).

Farmer et al., "Biochemical Identification of New Species and Biogroups of Enterobacteriaceae Isolated from Clinical Specimens," *J. Clin. Microbiol.*, 21:46–76 (1985).

"Characteristics of GELRITE Gels," in GELRITE™. Gellan Gum Thermal–Reversible Gelling Agent, Commercial Development CD–26, Kelco, San Diego.

Williams et al., "Numerical Classification of Streptomyces and Related Genera," *J. Gen. Microbiol.*, 129:1743–1813 (1983).

* cited by examiner

PANEL A

PANEL B

PANEL C

COMPARATIVE PHENOTYPE ANALYSIS

The present application is a Continuation of U.S. patent application Ser. No. 09/574,087, filed May 18, 2000, which is a continuation of U.S. patent application Ser. No. 09/333,802 filed Jun. 15, 1999, abandoned, which is a Continuation-in-Part of U.S. patent application Ser. No. 09/098,066, filed Jun. 16, 1998 now U.S. Pat. No. 6,046,021, which is a Continuation-in-Part of U.S. patent application Ser. No. 08/762,656, filed Dec. 9, 1996 now U.S. Pat. No. 5,882,882 which is a Continuation-in-Part of U.S. patent application. Ser. No. 08/421,377, filed Apr. 12, 1995 now U.S. Pat. No. 5,627,045, issued May 6, 1997.

FIELD OF THE INVENTION

The present invention relates to growing and testing any cell type in a multitest format which utilizes a gel forming matrix for the rapid screening of clinical and environmental cultures. The present invention is suited for the characterization of commonly encountered microorganisms (e.g., *E. coli, S. aureus,* etc.), as well as commercially and industrially important organisms from various and diverse environments (e.g., the present invention is particularly suited for the growth and characterization of the actinomycetes and fungi). The present invention is also particularly suited for analysis of phenotypic differences between strains of organisms, including cultures that have been designated as the same genus and species. In addition, the present invention provides methods and compositions for the phenotypic analysis and comparison of eukaryotic (e.g., fungal and mammalian), as well as prokaryotic (e.g., eubacterial and archaebacterial) cells.

BACKGROUND OF THE INVENTION

Ever since the golden age of microbiology in the era of Koch and Pasteur, methods for identification of microorganisms have been investigated. Koch's experimental proof that microorganisms cause disease in the early 1800's, provided the impetus to study methods to grow and characterize harmful, as well as beneficial microorganisms. Koch's early experiments to determine the etiology of infectious diseases, led to methods for cultivation of microorganisms on the surface of solid media (e.g., potato slices, see Koch, "Methods for the Study of Pathogenic Organisms," in T. D. Brock, *Milestones in Microbiology,* American Society for Microbiology, 1961, pp. 101–108; originally published as: "Zur Untersuchug von pathogenen Organismen," Mittheilungen aus dem Kaiserlichen Gesundheitsamte 1:1–48 [1881]). These studies eventually led to the development of agar as a culture medium component useful for producing solid media for growing isolated colonies of bacteria. To this day, isolated colonies are required (i.e., "pure cultures") to biochemically identify organisms.

The field of diagnostic and clinical microbiology has continued to evolve, and yet, there remains a general need for systems that provide rapid and reliable biochemical identifications of microorganisms. In particular, it has been very difficult to develop an identification system which is capable of identifying various diverse types of organisms, ranging from the common isolate *Escherichia coli* to the less commonly encountered actinomycetes and fungi.

Methods and identification systems to characterize microorganisms widely used in industry for production of food and drink (e.g., beer, wine, cheese, yogurt, etc.), the is production of antibiotics (e.g., penicillin, streptomycin, etc.), bioremediation of oil spills, biological control of insect pests (e.g., *Bacillus thuringiensis*), and the production of recombinant proteins, are still needed. In addition, very few identification methods and systems have been developed for environmental use and there remains a need for simple and generally useful identification methods of many organisms. In particular, methods for identification and growth of the actinomycetes are lacking.

I. The Actinomycetes

The actinomycetes (members of the order Actinomycetales) include a large variety of organisms that are grouped together on the basis of similarities in cell wall chemistry, microscopic morphology, and staining characteristics. Nonetheless, this is a very diverse group of organisms. For example, genera within this group range from the strict anaerobes to the strict aerobes. Some of these organisms are important medical pathogens, while many are saprophytic organisms which benefit the environment by degrading dead biological or organic matter. While many of these organisms grow optimally at temperatures common in the environment (e.g., 25–27° C.), some organisms are quite capable of growing at the body temperature of most mammals (e.g., approximately 35–37° C.). However, two genera of medically important actinomycetes (Thermomonospora and Micropolyspora) are true thermophiles, capable of growing at temperatures ranging to 50° C.

Colonies may be bacterium-like (i.e., ranging from butyrous to waxy and glabrous), or fungus-like (i.e., heaped, leathery, membranous colonies that are covered with aerial hyphae). Many actinomycetes exhibit filamentous growth with mycelial colonies, and some actinomycetes cause chronic subcutaneous granulomatous abscesses much like those caused by fungi. Because of these similarities, the actinomycetes were long-regarded as fungi, rather than bacteria (see e.g., G. S. Kobayashi, "Actinomycetes: The fungus-like bacteria," in B. D. Davis et al., *Microbiology,* 4th ed., J. B. Lippincott Co., New York, 1990), pp. 665–671).

Despite their similarities with the fungi, the actinomycetes have typical prokaryotic characteristics in terms of nucleoid and cell wall structure, antimicrobial sensitivity, the absence of sterols, motility by means of simple flagella, and long filaments of the diameter of bacteria (approximately 1 $\mu$m, compared to the larger fungal hyphae). Microscopically, the morphology of the aerobic actinomycetes varies widely between genera and species, although they are generally observed as gram-positive rods or branching filaments. Some genera never progress beyond a typical bacterium-like coccoid or bacillary form (e.g., Rhodococcus sp.), while others form filaments with extensive branching (e.g., Nocardia, Streptomyces, Actinomadura, and Nocardiopsis). Most are non-motile in their vegetative phase of growth. However, some genera tend to form branched filaments which eventually fragment into motile, flagellated cells (e.g., Oerskovia sp.) (see e.g., G. Land et al., "Aerobic pathogenic Actinomycetales," in A. Balows et al., *Manual of Clinical Microbiology,* 1991, pp. 340–359).

Most of the actinomycetes form spores, with the type of spore formation serving as a phylogenetic and taxonomic tool for separating the organisms into groups. The actinomycetes are highly diverse, with at least ten subgroups. They are also closely related to such organisms as the coryneforn group (e.g., Corynebacterium sp.), the propionic acid bacteria (e.g., Propionibacterium sp.), and various obligate anaerobes (e.g., Bifidobacterium, Acetobacterium, Butyrvibrio, and Thermoanaerobacter). The following table lists the organisms included in the suprageneric groups of actinomycetes as set forth in the most recent edition of *Bergey's Manual*, vol. 4, (Stanley T. Williams, editor of vol. 4; John G. Holt, editor in chief, *Bergey's Manual® of Systematic Bacteriology*, Williams & Wilkins, pp. 2334–2338 [1989]).

TABLE 1

Actinomycetes Groups

| Number | Group | Representative Groups/Genera | |
|---|---|---|---|
| I | Actinobacteria | Group A: | Agromyces, Aureobacterium |
| | | Group B: | Arthrobacter, Rothia |
| | | Group C: | Cellulomonas, Oerskovia |
| | | Group D: | Actinomyces, Arcanobacterium |
| | | Group E: | Arachnia, Pimelobacter |
| | | Group F: | Brevibacterium |
| | | Group G: | Dermatophilus |
| II | Actinoplanetes | Actinoplanes, Ampullariella, Micromonospora | |
| III | Maduromycetes | *Actinomadura pusilla* group, Microbispora, Streptosporangium | |
| IV | Micropolysporas | Actinopolyspora, Faenia, Saccharomonospora | |
| V | Multilocular Sporangia | Frankia, Geodermatophilus | |
| VI | Nocardioforms | Nocardia, Rhodococcus, Caseobacter | |
| VII | Nocardioides | Nocardiodes | |
| VIII | Streptomycetes | Streptomyces, Streptoverticillium, Kineosporia | |
| IX | Thermomonosporas | Thermomonospora, Nocardiopsis, Actinomadura madurae group | |
| X | Other Genera | Glycomyces, Kitasatosporia Spirillospora, Thermoactinomyces | |

Although these organisms may often be identified to the genus level based on their morphology at the time of primary isolation, organisms that have been repeatedly transferred in the laboratory often do not retain their typical morphologic characteristics and must be identified biochemically, or by analysis of their membrane fatty acid composition. Serological methods for identification and differentiation are rarely used, due to the extensive degree of cross-reactivity among the actinomycetes (See e.g., G. S. Kobayashi, supra, at p. 666).

II. Importance of the Actinomycetes as Pathogens

Many of these organisms are soil-dwellers, with relatively little pathogenic capabilities. Indeed, the actinomycetes are among the most abundant of organisms in the soil, where they serve the important function of breaking down proteins, cellulose, and other organic matter. Nonetheless, some Actinomyces, Nocardia, and Streptomyces species are associated with diseases of medical and veterinary importance, especially in immunocompromised individuals. The spectrum of disease caused by the actinomycetes is extremely broad, with pathology that is dependent upon a combination of organism type, tissue involved, and the immune status of the host. In immunocompetent humans, the most common diseases are a non-invasive, acute or chronic allergic respiratory syndrome (e.g., farmer's lung), and mycetoma. In immunocompromised individuals, infection often begins in the lung as an acute to chronic suppurative process, which may progress to cavitation and multi-lobular pulmonary disease. In these patients, infection may spread to other organ systems. Importantly, these organisms have a predilection for the central nervous system.

Several species of Actinomyces have been associated with actinomycosis in humans and other animals, with *A. israelii* being the most common human isolate, and *A. bovis* the most common cattle isolate. Actinomycosis is usually characterized by chronic, destructive abscesses of connective tissues. Abscesses expand into the neighboring tissues and eventually produce burrowing, tortuous sinus tracts to the surface of the skin, where purulent material is discharged. In cattle, the lesions are characteristically large abscesses of the lower jaw (hence the common name of the disease, "lumpy jaw"), usually with extensive bone destruction. As with most saprophytic organisms that occasionally cause disease, actinomycosis is not transmissible from person to person, nor between humans and other animals. Indeed, it is difficult to establish infection in laboratory animals.

For in vitro growth in the laboratory, these pathogenic organisms tend to be microaerophilic (e.g., require a decreased oxygen tension for optimum growth), require rich growth media, optimum incubation temperatures of 37° C., and about 7 days of incubation. Although actinomycetes are soil organisms, actinomycosis is usually caused by endogenous organisms that have colonized the individual, rather than organisms from the environment. The organism is usually a conmuensal, which can be cultured from the tonsils of most humans, and is almost always present in teeth and gum scrapings. The conditions that lead to invasiveness are not well characterized, but may be multi-factorial, as actinomycotic infections are often mixed, with various organisms (e.g., *Haemophilus actinomycetemcomitans, Eikenella corrodens,* Fusobacterium, and Bacteroides) also present.

In contrast to the Actinomyces, diseases due to Nocardia sp. are associated with infection of the individual with soil organisms, rather than endogenous comnnensals. Nocardia are among the most clinically important actinomycetes, as they are responsible for the majority of disease associated with this group of organisms. Indeed, the term "nocardiosis" is often used synonymously for pulmonary and disseminated infection caused by any of the aerobic actinomycetes (see e.g., G. Land et al., "Aerobic Pathogenic Actinomycetales," in A. Balows et al., *Manual of Clinical Microbiology,* 5th ed., American Society for Microbiology, Washington, D.C., 1991, pages 340–359).

There are two common forms of disease associated with Nocardia sp., namely, pulmonary nocardiosis resulting from inhalation of the organism, and mycetoma, which is characterized by chronic subcutaneous abscesses resulting from contamination of skin wounds. These infections are usually serious, especially as they are frequently seen in association with immunosuppression or chronic underlying diseases (e.g., carcinoma, chronic granulomatous disease, Hodgkin's disease, and leukemia). Once clinically evident, the progression of nocardiosis tends to be progressive and fatal, with approximately 50% of patients dying, even with aggressive therapy (see e.g., G.S. Kobayashi, "Actinomycetes: The Fungus-Like Bacteria, in B. D. Davis et al. (eds.), *Microbiology,* 4th ed., J. B. Lippincott Co., Philadelphia [1990], pages 665–671).

The Nocardia are aerobic organisms which grow on relatively simple media over a wide temperature range. As with the mycobacteria, growth in liquid media usually results in the production of a dry, waxy pellicle on the surface of the media.

The two species most commonly associated with human disease, *N. brasiliensis* and *N. asteroides,* share many other characteristics with the mycobacteria. For example, they are somewhat acid-fast, more easily stained with fuchsin, and their cell walls contain components characteristic of mycobacteria and corynebacteria (e.g., mycolic acid residues). Unlike the great majority of organisms, the somewhat harsh methods used to isolate mycobacteria (e.g., treatment of samples with N-acetyl-L-cysteine, and sodium hydroxide)

are often successful for isolation of Nocardia. Extensive serologic cross-reactions in agglutination and complement fixation tests further indicate the relatedness of these groups of organisms.

The Streptomyces are also sometimes associated with actinomycotic abscesses. Mycetomas caused by streptomycetes are clinically indistinguishable from those caused by other actinomycetes. However, identification of these organisms can be critical, as they are generally not susceptible to antimicrobial agents. Therefore, treatment often entails surgical removal of the affected area or amputation.

Other members of the actinomycetes are capable of causing disease, including allergic respiratory disease ("farmer's lung"), which occurs in agricultural workers who inhale dust from moldy plant material. This syndrome has been associated with at least three thermophilic actinomycetes (*Thermopolyspora polyspora, Micromonospora vulgaris,* and *Micropolyspora faeni*). This disease is very similar to that caused by inhalation of allergens produced by various fungi, particularly Aspergillus sp.

In addition to the pathogenic potential of this group of organisms, there is also great interest in the particular genera which produce antimicrobial compounds.

III. Industrial Importance of the Actinomycetes

Ever since Waksman isolated actinomycin in 1940, and streptomycin in 1943, the streptomycetes have attracted a large amount of attention (see e.g., G. S. Kobayashi, et al., at p. 671). Thousands of soil samples collected world-wide have resulted in the identification of over 90% of the therapeutically useful antibiotics (see e.g., G. S. Kobayashi, "Actinomycetes: The Fungus-Like Bacteria, in B. D. Davis et al. (eds.), *Microbiology,* 4th ed., J. B. Lippincott Co., Philadelphia [1990], pages 665–671). The interest in improving antibiotic qualities and yields has resulted in various studies on this group of organisms, including improved methods for their growth and characterization.

It is important that strains be differentiated in screening programs to identify antibiotic activities, so that redundant testing is avoided. In addition, differentiation facilitates determination of taxonomic relationships which may lead to other organisms with promising activities. Unfortunately, testing of these organisms is often very difficult. Because they grow as filaments, they have a strong tendency to form clumps of mycelia which makes them much more difficult to handle, both in liquid cultures and on solid or semi-solid agar media. Furthermore, because of their complex life cycle which involves sporulation and germination, it is very difficult to obtain cultures which perform consistently in metabolic and biochemical testing programs. In addition, the presence of spores and the potential for their inhalation, represents a safety hazard to personnel responsible for the cultivation and characterization of these organisms, especially in settings where large-scale growth is necessary (e.g., antimicrobial production).

These growth characteristics also contribute to the difficulties associated with determining the susceptibility of the actinomycetes to antimicrobial compounds. The most frequently used testing methods are a modified Kirby-Bauer disk diffusion method agar dilution, and a minimal inhibitory concentration (MIC) method (see e.g., G. Land et al., "Aerobic Pathogenic Actinomycetales," in A. Balows et al., *Manual of Clinical Microbiology.* 5th ed., American Society for Microbiology, Washington, D.C., [1991], at p. 356). However, the success of these methods is contingent upon the production of a homogenized suspension for use as a standardized inoculum. Most commonly, agitation with sterile glass beads or a tissue homogenizer is used to prepare a homogenous suspension that can then be diluted to a 0.5 McFarland standard prior to inoculating the test media (see e.g., G. Land et al., "Aerobic Pathogenic Actinomycetales," in A. Balows et al., *Manual of Clinical Microbiology,* 5th ed., American Society for Microbiology, Washington, D.C., 1991, pages 340–359). These methods involving physical homogenization are very labor-intensive and tedious, and they result in damage, fragmentation, and death of some fraction of the cells. Furthermore, the additional manipulation required to produce a homogenous suspension prior to inoculation increases the risk of contamination of laboratory personnel and the laboratory environment.

Therefore, what is needed is a safe, reliable, easy-to-use system for the characterization and testing of medically and industrially important organisms, including but not limited to organisms such as the actinomycetes. In particular what is need is a rapid method that is readily automatable and useful in various settings (e.g., clinical, veterinary and environmental laboratories, and industry). Methods and compositions are also needed for high-volume, reliable analysis of strain differences between organisms.

SUMMARY OF THE INVENTION

The present invention relates to growing and testing any cell type in a multitest format which utilizes a gel forming matrix for the rapid screening of clinical and environmental cultures. In particular, the present invention is suited for the characterization of commonly encountered microorganisms (e.g., *E. coli, S. aureus,* etc.), as well as commercially and industrially important organisms from various and diverse environments. For example, the present invention is particularly suited for the growth and characterization of bacteria, as well as the actinomycetes and fungi (e.g., yeasts and molds).

In one embodiment, the present invention provides methods for testing microorganisms comprising the steps of: providing a testing means comprising redox purple and one or more test substrates; introducing microorganisms into the testing means; and detecting the response of the microorganism to the one or more test substrates. In a preferred embodiment, the testing substrates are selected from the group consisting of carbon sources and antimicrobials.

In an alternate embodiment, the testing means fiuther comprises one or more gel-initiating agents. In a preferred embodiment, the gel-initiating agent comprises cationic salts. In another alternative embodiment, the testing means further comprises one or more gelling agents. In a preferred embodiment, the microorganisms are in an aqueous suspension. In another preferred embodiment, the aqueous suspension fuirther comprises one or more gelling agents. It is contemplated that various gelling agents will be used with the present invention, including, but not limited to agar, gellan gum (e.g., Gelrite™ and Phytagel™), carrageenan, and alginic acid.

In one embodiment of the method, the microorganisms are bacteria, while in another embodiment, the microorganisms are fungi. It is also contemplated that the methods of the present invention will be used with members of the Order Actinomycetales.

It is contemplated that various testing means will be used in the present invention. In one preferred embodiment, the testing means comprises at least one microplate (e.g., MicroPlate™ microtiter plates, available from Biolog), while in an alternative embodiment, the testing means comprises at least one miniaturized testing plates or cards (e.g., MicroCard™ test cards, available from Biolog). In yet another embodiment, the testing means comprises at least one petri plate.

The present invention also provides a kit, comprising redox purple and one or more test substrates. In a preferred embodiment, the test substrates are selected from the group consisting of carbon sources and antimicrobials. In another preferred embodiment, the kit further comprises one or more gel-initiating agents. In a particularly preferred embodiment, the gel initiating agent comprises cationic salts. In an alternative preferred embodiment, the kit further comprises one or more gelling agents. In another preferred embodiment, the gelling agent is selected from the group consisting of agar, gellan gum (e.g., Gelrite™ and/or Phytagel™), carrageenan, and alginic acid.

In another embodiment, the kit further comprises a suspension of microorganisms. In one preferred embodiment, the kit further comprises a testing means. It is contemplated that various testing means formats will be used successfully in various embodiments of the kits of the present invention, including microplates (e.g., MicroPlate™ microtiter plates), miniaturized testing plates or cards (e.g., MicroCard™ miniaturized test cards), petri plates, and any other suitable support in which the testing reaction can occur.

In yet another embodiment, the present invention provides a kit, comprising redox purple and one or more gelling agents. It is contemplated that various gelling agents will be used successfully in the various embodiments of the kits of the present invention, including but not limited to agar, gellan gum (e.g., Gelrite™ and/or Phytagel™), carrageenan, and alginic acid. In one preferred embodiment, the kit further comprises one or more gel-initiating agents. In a particularly preferred embodiment, the gel-initiating agent comprises cationic salts. In an alternative embodiment, the kit frther comprises a suspension of microorganisms.

In an alternative embodiment, the kit further comprises one or more test substrates. It is contemplated that the test substrates included in the kit of the present invention be selected from the group consisting of carbon sources and antimicrobials.

In yet another embodiment, the kit further comprises a testing means. It is contemplated that various testing means formats will be used successfully in various embodiments of the kits of the present invention, including microplates (e.g., MicroPlate™ microtiter plates), miniaturized testing plates or cards (e.g., MicroCard™ miniaturized test cards), petri plates, and any other suitable support in which the testing reaction can occur.

The present invention describes test media and methods for the growth, isolation, and presumptive identification of microbial organisms. The present invention contemplates compounds and formulations, as well as methods particularly suited for the detection and presumptive identification of various diverse organisms.

In order to characterize or identify organisms present in a sample, the present invention combines a gel-forming suspension with microorganisms that are already in the form of a pure culture. This is in contrast to the traditional pour plate method which involves heated agar and a sample that contains a mixed culture (see e.g., J. G. Black, *Microbiology: Principles and Applications,* 2d ed., Prentice Hall, Englewood Cliffs, N.J., p. 153 [1993]; and American Public Health Association, *Standard Methods for the Examination of Water and Wastewater,* 16th ed., APHA, Washington, D.C., pp. 864–866 [1985]).

It is also in contrast to the pour plate method of Roth (U.S. Patent Nos. 4,241,186, and 4,282,317), which utilizes a solidifying pectin substance. In the present invention, colloidal gel-forming substances are used at low concentrations, forming soft gels or viscous colloidal suspensions that do not need to, and in fact work best, when not completely solidified into a rigid gel.

In one embodiment, the present invention provides a method for introducing microorganisms into a testing device, comprising the steps of providing a testing device comprising a plurality of testing wells or compartments, wherein each compartment contains one or more gel-initiating agents; preparing a suspension comprising a pure culture of microorganisms and an aqueous solution containing a gelling agent, under conditions such that the suspension remains ungelled; and introducing the suspension into the testing device under conditions such that the suspension contacts the gel-initiating agents present in the compartments and results in the production of a gel or colloidal matrix.

In another embodiment, the present invention provides a method for testing microorganisms comprising the steps of providing a testing device comprising a plurality of testing compartments, wherein the compartments contain a testing substrate and one or more gel-initiating agents; preparing a suspension comprising a pure culture of microorganisms and an aqueous solution comprising a gelling agent under conditions such that the suspension remains ungelled; introducing the suspension into the compartments of the testing device under conditions such that the suspension forms a gel matrix within the compartment; and detecting the response of the microorganisms to the testing substrate. In one preferred embodiment, the testing device is a microplate (e.g., MicroPlate™ microtiter plates).

It is contemplated that the microorganisms tested in this method will be bacteria, including members of the Order Actinomycetales, or fungi (e.g., yeasts and molds).

In one embodiment, the gelling agent is selected from the group consisting of gellan gum (e.g., Gelrite™ and/or Phytagel™), carrageenan, and alginic acid. In a particularly preferred embodiment, the gelling agent is carrageenan which contains predominantly iota-carrageenan. In one embodiment, the gel-initiating agent comprises cationic salts.

In one embodiment, the testing substrates are selected from the group consisting of carbon sources and antimicrobials. In yet another embodiment, the method further includes a calorimetric indicator, wherein the colorimetric indicator is selected from the group consisting of chromogenic substrates, oxidation-reduction indicators, and pH indicators.

In yet another embodiment, the present invention encompasses a kit for growth and identification of microorganisms comprising: a testing device comprising a plurality of testing compartments containing one or more gel-initiating agents; and an aqueous solution comprising a gelling agent. In one preferred embodiment, the testing compartments ether contain testing substrates, such as carbon sources and antimicrobials. In one embodiment, the gel-initiating agent comprises cationic salts.

In one embodiment of this kit, the testing device is a microplate (e.g., MicroPlate™ microtiter plates). In a preferred embodiment, the kit contains a gelling agent that is selected from the group consisting of gellan gum (e.g., Gelrite™ and/or Phytagel™), carrageenan, and alginic acid. In one preferred embodiment, the gelling agent is a carrageenan which predominantly contains the iota form of carrageenan. In one embodiment, the gel-initiating agent comprises cationic salts.

It is contemplated that the kit of the present invention will be used with microorganisms such as bacteria, including members of the Order Actinomycetales, as well as fungi (e.g., yeasts and molds).

It is also contemplated that the kit will also include a calorimetric indicator selected from the group consisting of chromogenic substrates, oxidation-reduction indicators, and pH indicators.

In an alternative embodiment, the present invention comprises a kit for characterizing and identifying microorganisms comprising: a testing device containing a plurality of compartments, wherein the compartments contain one or more gel-initiating agents and one or more testing substrates, wherein the testing substrates are selected from the group consisting of antimicrobials and carbon sources and an aqueous suspension comprising a gelling agent.

In one embodiment of this kit, the testing device is a microplate (e.g., MicroPlate™ microtiter plates), while in other embodiments, the testing device is a miniaturized testing plate or card (e.g., MicroCard™ miniaturized testing cards). In a preferred embodiment, the kit contains a gelling agent that is selected from the group consisting of gellan gum (e.g., Gelrite™ and/or Phytagel™), carrageenan, and alginic acid. In one preferred embodiment, the gelling agent is a carrageenan which predominantly contains the iota form of carrageenan. In one embodiment, the gel-initiating agent comprises cationic salts.

It is contemplated that the kit of the present invention will be used with microorganisms such as bacteria, including members of the Order Actinomycetales, as well as fungi (e.g., yeasts and molds).

It is also contemplated that the kit will include a colorimetric indicator selected from the group consisting of chromogenic substrates, oxidation-reduction indicators, and pH indicators.

The present invention also provides methods for comparing the function of a gene in at least two cell preparations, comprising the steps of: providing a testing device comprising a plurality of testing wells, wherein the wells contain a testing substrate and one or more gel-initiating agents; preparing a first suspension comprising a first cell preparation, in an aqueous solution comprising a gelling agent, and a second suspension comprising a second cell preparation in an aqueous solution comprising a gelling agent, under conditions such that the first and second suspensions remain ungelled; introducing the first and second suspension into the wells of the testing device under conditions such that the first and second suspensions form a gel matrix within the wells, such that the first and second cell preparations are within the gel matrix; detecting the response of the first and second cell preparations to the testing substrate; and comparing the response of the first and second cell preparations. In some embodiments, the first and second cell preparations comprise microorganisms selected from the group consisting of bacteria and fungi. In yet other embodiments, the first and second cell preparations contain cells of the same genus and species, while in still other embodiments, the first and second cell preparations contain cells that differ in one or more genes.

In alternative embodiments of the methods, the gelling agent is selected from the group consisting of gellan gum (e.g., Gelrite™ and/or Phytagel™), carrageenan, and alginic acid. In further embodiments, the testing substrates are selected from the group consisting of carbon sources, nitrogen sources, sulfur sources, phosphorus sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and antimicrobials. Indeed, it is not intended that the present invention be limited to any particular testing substrates, as it is contemplated that any testing substrate suitable for use with the present invention will be utilized. In still other embodiments, the gel-initiating agent comprises cationic salts. In some preferred embodiments, the methods further comprise a calorimetric indicator. In particularly preferred embodiments of the methods, the colorimetric indicator is selected from the group consisting of chromogenic substrates, oxidation-reduction indicators, and pH indicators. In some particularly preferred embodiments, the oxidation-reduction indicator is tetrazolium violet, while in other embodiments, the oxidation-reduction indicator is redox purple. In yet other preferred embodiments, the testing device is at least one microplate (e.g., MicroPlatem microtiter plates), while in other preferred embodiments, the testing device is at least one miniaturized testing plate or card (e.g., MicroCard™ testing cards). In further preferred embodiments, the response is a kinetic response.

The present invention also provides kits suitable for determining the phenotype of at least two organisms, comprising: a testing device containing a plurality of wells, wherein the wells contain one or more gel-initiating agents and one or more testing substrates; a first aqueous suspension comprising a gelling agent; and a second aqueous suspension comprising a gelling agent.

In one preferred embodiment of the kits, the testing substrates are selected from the group consisting of carbon sources, nitrogen sources, sulfur sources, phosphorus sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and antimicrobials. Indeed, it is not intended that the present invention be limited to any particular testing substrates, as it is contemplated that any testing substrate suitable for use with the present invention will be utilized. In alternative preferred embodiments of the kits, the gelling agent is selected from the group consisting of gellan gum (e.g., Gelrite™ and/or Phytagel™), carrageenan, and alginic acid. In still other embodiments of the kit, the gel initiating agent comprises cationic salts. In some particularly preferred embodiments, the testing device further comprises a colorimetric indicator selected from the group consisting of chromogenic substrates, oxidation-reduction indicators, and pH indicators. In alternate preferred embodiments, the oxidation-reduction indicator is tetrazolium violet, while in other embodiments, the oxidation-reduction indicator is redox purple.

The present invention further provides methods and compositions for extrapolating the functions of genes or genetic sequences in various cell types. For example, the present invention provides methods for extrapolating the function of genes or genetic sequences in eukaryotic cells. In some embodiments, microbial genomes are examined to identify sequences that are homologous to the gene(s) or genetic sequence(s) of interest in the eukaryotic cell. Then, mutations are introduced into the homologous microbial gene. Next, the phenotypes of the wild-type and mutant microbial cells are analyzed and/or compared, as desired. In other embodiments, the functions of the microbial and eukaryotic genes are compared by utilizing genetic engineering methods to prepare transferable expression vectors (e.g., plasmids, phages, etc.) containing the eukaryotic gene(s) or genetic sequence(s) of interest. This expression vector is transferred into and expressed in a microbial host cell. The phenotype of the host microbial cell (ie., the cell containing the expression vector) and untransformed microbial cells (i.e., control cells comprising the same microbial cell line, but not containing the expression vector) are then analyzed and/or compared, as desired. In further embodiments, the vector comprises eukaryotic genes that have been modified (i.e., the genes are modified such that they are not the same as the wild type gene sequences).

The present invention also provides methods for comparing at least two cell preparations, comprising the steps of: providing a testing device comprising a plurality of testing wells, wherein the wells contain at least one test substrate selected from the group consisting of nitrogen sources, phosphorus sources, sulfur sources, and auxotrophic supplements; preparing a first suspension comprising a first cell preparation in an aqueous solution, and a second suspension comprising a second cell preparation in an aqueous solution; introducing the first and second suspensions into the wells of the testing device; detecting the response of the first and second cell preparations to the testing substrate; and comparing the response of the first and second cell preparations. In some embodiments of these methods, the first and second cell preparations comprise microorganisms selected from the group consisting of bacteria and fungi. In still other embodiments, the first and second cell preparations contain cells of the same genus and species, while in other embodiments, the first and second cell preparations contain cells that differ in one or more genes.

In certain preferred embodiments, the testing substrates further comprise substrates selected from the group consisting of carbon sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and antimicrobials. In further embodiments, the method further comprises a calorimetric indicator. In some preferred embodiments, the colorimetric indicator is selected from the group consisting of chromogenic substrates, oxidation-reduction indicators, and pH indicators. In particularly preferred embodiments, the oxidation-reduction indicator is tetrazolium violet or redox purple. In yet other preferred embodiments, the testing device is at least one microplate (e.g., MicroPlate™ microtiter plates), while in other preferred embodiments the testing device is a miniaturized test plate or card (e.g., MicroCard™ miniaturized testing cards). In still other embodiments, the response is a kinetic response.

The present invention also provides methods for comparing the function of a gene in at least two cell preparations, comprising the steps of: providing a testing device comprising a plurality of testing wells, wherein the wells contain one or more gel-initiating agents, and at least one testing substrate selected from the group consisting of nitrogen sources, phosphorus sources, sulfur sources, and auxotrophic supplements; preparing a first suspension comprising a first cell preparation, in an aqueous solution comprising a gelling agent, and a second suspension comprising a second cell preparation in an aqueous solution comprising a gelling agent, under conditions such that the first and second suspensions remain ungelled; introducing the first and second suspensions into the wells of the testing device under conditions such that the first and second suspensions form a gel matrix within the wells, such that the first and second cell preparations are within the gel matrix; detecting the response of the first and second cell preparations to the testing substrate; and comparing the response of the first and second cell preparations. In some embodiments, the first and second cell preparations comprise microorganisms selected from the group consisting of bacteria and fungi, while in other embodiments, the first and second cell preparations contain cells of the same genus and species. In still other embodiments, the first and second cell preparations contain cells that differ in one or more genes.

In some embodiments of the methods, the testing substrates further comprise substrates selected from the group consisting of carbon sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and antimicrobials. In still other embodiments, the gelling agent is selected from the group consisting of gellan gum (e.g., Gelrite™ and/or Phytagel™), carrageenan, and alginic acid. In yet other embodiments, the gel-initiating agent comprises cationic salts. In some preferred embodiments, the method further comprises a calorimetric indicator. In some embodiments, the colorimetric indicator is selected from the group consisting of chromogenic substrates, oxidation-reduction indicators, and pH indicators. In some particularly preferred embodiments, the oxidation-reduction indicator is tetrazolium violet, while in other preferred embodiments, the oxidation-reduction indicator is redox purple. In yet other preferred embodiments, the testing device is at least one microplate (e.g., MicroPlate™ microtiter plates), while in other preferred embodiments the testing device is a mniniaturized test plate or card (e.g., MicroCard™ miniaturized testing cards). In still other embodiments, the response is a kinetic response.

The present invention also provides kits for determining the phenotype of at least two organisms, comprising: a testing device containing a plurality of wells, wherein the wells contain one or more testing substrates selected from the group consisting of nitrogen sources, phosphorus sources, sulfur sources, and auxotrophic supplements; a first aqueous suspension; and a second aqueous suspension. In some embodiments, the wells of the testing device furter contain one or more gel-initiating agents, the first aqueous suspension further comprises a first gelling agent, and the second aqueous suspension further comprises a second gelling agent. In still other embodiments, the testing substrates further comprise substrates selected from the group consisting of carbon sources, amino peptidase substrates, carboxy peptidase substrates, oxidizing agents, reducing agents, mutagens, amino acid analogs, sugar analogs, nucleoside analogs, base analogs, dyes, detergents, toxic metals, inorganics, and antimicrobials. In yet other embodiments, the gelling agent is selected from the group consisting of gellan gum (e.g., Gelrite™ and/or Phytagel™), carrageenan, and alginic acid. In further embodiments, the gel initiating agent comprises cationic salts. In still further embodiments, the testing device luger comprises a calorimetric indicator. In some preferred embodiments, the colorimetric indicator is selected from the group consisting of chromogenic substrates, oxidation-reduction indicators, and pH indicators. In some preferred embodiments, the oxidation-reduction indicator is tetrazolium violet, while in other preferred embodiments, the oxidation-reduction indicator is redox purple. In yet other preferred embodiments, the testing device is at least one microplate (e.g., MicroPlate™ microtiter plates), while in other preferred embodiments the testing device is a miniaturized test plate or card (e.g., MicroCard™ miniaturized testing cards). In still other embodiments, the response is a kinetic response.

GENERAL DESCRIPTION OF THE INVENTION

Figure 1:
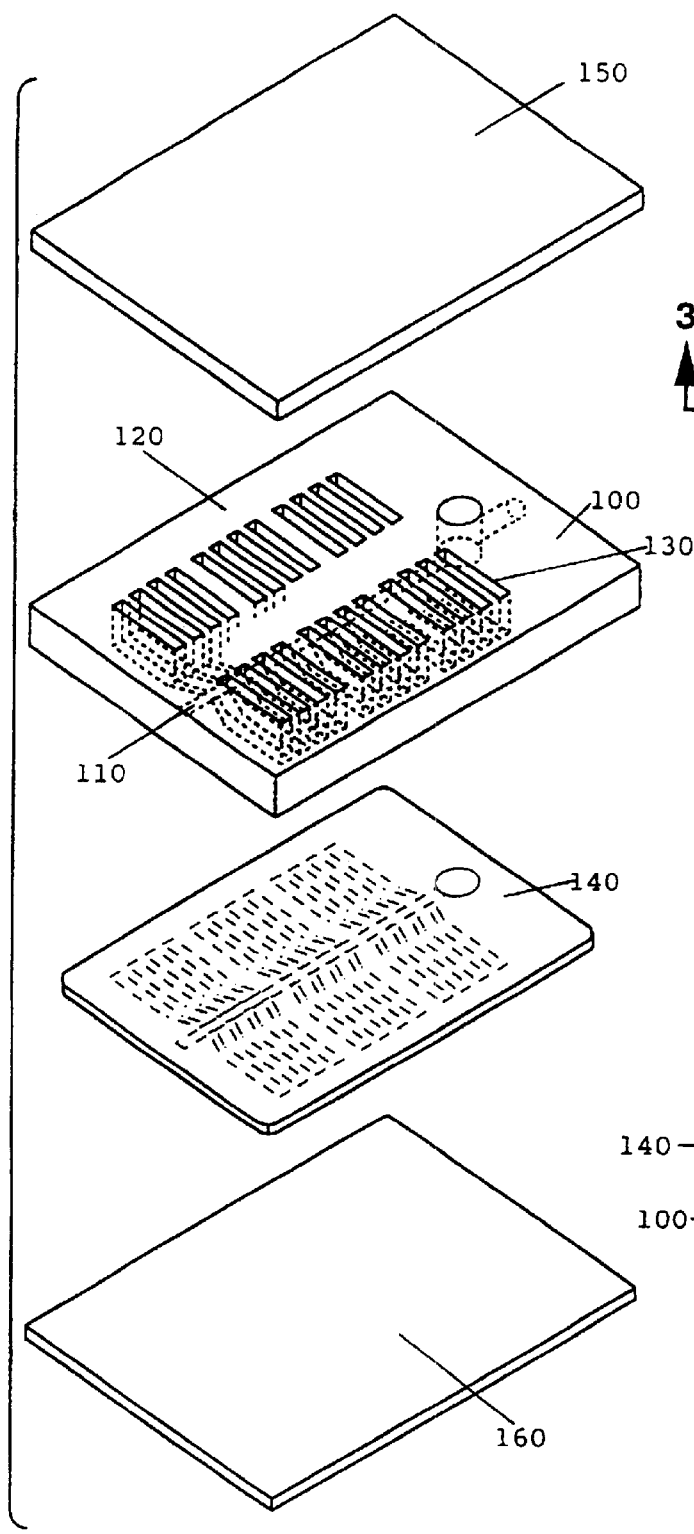
FIG. 1 is an exploded perspective view of one embodiment of the device of the present invention.
Figure 2:
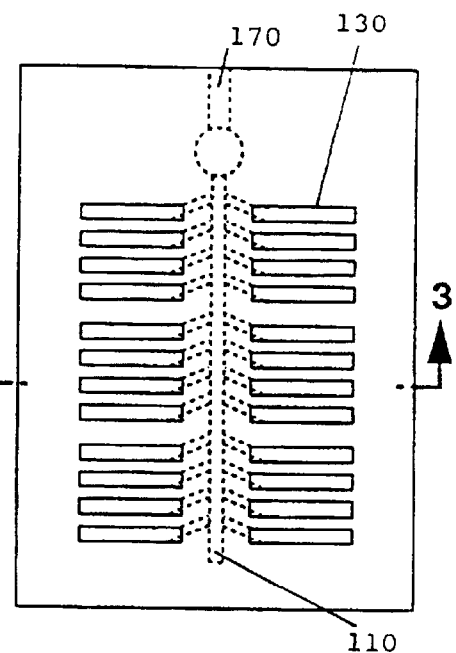
FIG. 2 is a top plan view of the device shown in FIG. 1.
Figure 3:
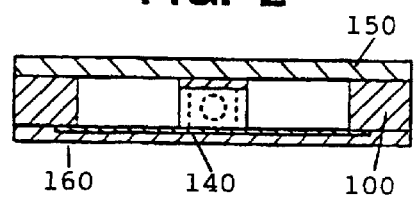
FIG. 3 is a cross-sectional view of the device shown in FIG. 2 along the lines of 3—3.
Figure 4:
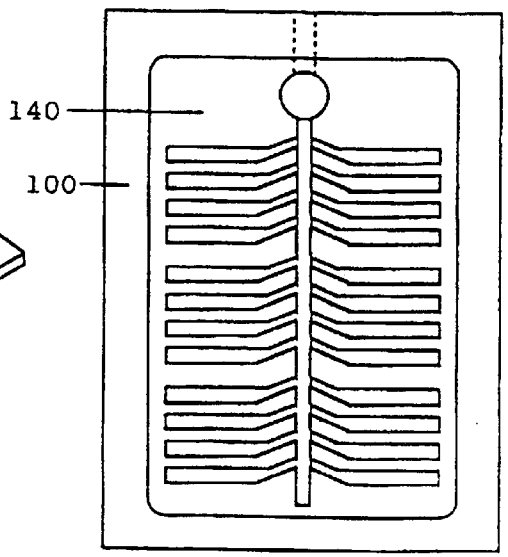
FIG. 4 is a bottom plan view of the device shown in FIG. 1.

The present invention is based in part on the discovery that various cells (e.g., microbial strains) can be differentiated based on differential biochemical reactions. Surprisingly, it was determined during the development of the present invention that in some cases, the biochemical reactions work best when the cells are contained within a gel matrix. Thus, the present invention incorporates a multiple test format in a testing device, for presumptive and rapid microbiological screening of various clinical, veterinary, research, industrial and environmental specimens. It is also intended that the present invention will be useful for definitive identification and diagnosis. In preferred embodiments, the present invention is suitable for the comparative phenotype testing of microorganisms and other cells. It is intended that comparative phenotypic testing will find use in functional genomics (ie., whereby cells and/or microbial strains that differ in a defined set of genetic traits are compared). It is not intended that the invention be limited to a particular genus, species nor group of organisms. Indeed, it is also intended that the present invention will find use with cells of any type, including, but not limited to cells maintained in cell culture, cell lines, etc., including mammalian, plant, and insect cells. The compositions and methods of the present invention are particularly targeted toward some of the most economically important organisms, as well as species of clinical importance.

The present invention contemplates an indicator plate essentially similar in structure to microtiter plates ("microplates" or "MicroPlates™") which are commonly used in the art and commercially available from numerous scientific supply sources (e.g., Biolog, Fisher, etc.). It is contemplated that the present invention be used with various gelling agents, including but not limited to alginate, carrageenan, and gellan gum (e.g., Gelrite™ and/or Phytagel™).

Because the cells are trapped within the gel matrix, the present invention is a great improvement over standard microtiter plate testing methods in which liquid cultures are used. Unlike the liquid format, the gel matrix of the present invention does not spill from the microtiter plate, even if the plate is completely inverted. This safety consideration highlights the suitability of the present invention for use with organisms or other cells that are easily aerosolized. It is also contemplated that the present invention is highly useful in the educational setting, where safety is a primary concern. The present invention permits novices to work with bacteria and study their biochemical characteristics with a reduced chance of contamination, as compared to other testing systems. In addition, the present invention permits novices to work with infected cells (e.g., virally-infected cells harvested from cell cultures), with a reduced chance of contamination.

The gel matrix system of the present invention also offers other important advantages. For example, over incubation periods of several hours, cells will often sink to the bottom of testing wells and/or attach or clump to other cells, resulting in a non-uniform suspension of cells within the wells. This non-uniformity can result in a non-uniform response of the cells in the well. Clumping artifacts perturb the optical detection of cellular responses. Thus, because the present invention provides methods and compositions which trap the cells in a gel matrix within the wells, the cells are uniformly suspended, and have uniform access to nutrients and other compounds in the wells. Thus, the present invention serves to make this type of cell testing as reproducible and homogenous as possible. Furthermore, in natural settings, cells often grow attached to surfaces or in contact with other cells (e.g., in biofilms or monolayers). By providing contact between the cells and a semi-solid, gel support, the gel matrix of the present invention simulates the natural state of cell growth. In addition, the gel matrix decreases the diffusion of oxygen to the cells and helps protect them from oxidative damage.

As various cells may be characterized using the present invention, it is not intended that the choice of primary isolation or culture media be limited to particular formulae. In addition to commonly isolated organisms, the range of cell types that can be tested using the methods and compositions of the present invention includes cells that undergo complex forms of differentiation filamentation, sporulation, etc. For example, in one embodiment, organisms such as the actinomycetes are grown on an agar medium which stimulates the production of aerial conidia. This greatly facilitates the harvesting of organisms for inoculation in the present invention. However, it is not intended that the present invention be limited to actinomycetes. Indeed, the present invention provides methods and compositions for the testing of fungi (e.g., yeasts and molds), as well as bacteria other than actinomycetes. As with the actinomycetes, these organisms may be grown on any primary isolation or culture medium that is suitable for their growth, although it is preferred that the primary isolation or culture medium used promotes the optimal growth of the organisms. For cell lines and cell cultures (i.e., mammalian, plant, and/or insect cells maintained in vitro), the cells are grown in cell culture media (e.g., Eagle's Minimal Essential Medium, etc.), suitable for the cell growth.

In one embodiment, a microplate (e.g., a MicroPlate™ microtiter plate) format is used. In this embodiment, the gel-forming matrix containing suspended cells is used to inoculate the wells of a microplate or another receptacle. At the time of inoculation, the gel-forming matrix is in liquid form, allowing for easy dispensing of the suspension into the compartments. These compartments contain dried biochemicals and cations. Upon contact of the gel-forming matrix with the cations, the suspension solidifies to form a soft gel, with the cells evenly distributed throughout. This gel is sufficiently viscous or rigid that it will not fall out of the microplate should the plate be inverted.

In another embodiment, a microcard format is used. As shown in FIGS. 1–4, one embodiment of the device of the present invention comprises a housing (100) with a liquid entry port through which the sample is introduced. The housing further contains a channel (110) providing communication to a testing region (120) so that a liquid (not shown) can flow into a plurality of wells or compartments (130). The channel (110) is enclosed by the surface of a hydrophobic, gas-venting membrane (140) adapted for forming one surface of the wells (130) and attached to one side of the housing (100). The housing (100) can be sealed on its other side by a solid base (150). In other embodiments, a flexible tape (not shown) may be substituted for the solid base (150) or the solid base (150) may be molded so as to be integral with the housing (100).

After filling the device with the gel-formling matrix containing cells, (not shown) an optional non-venting material such as tape (e.g., polyester tape) (160) can be adhered to the outer surface of the gas-venting membrane (140) to seal it against evaporation of the gel matrix within the device through the gas-venting membrane. At the time of delivery, the gel-forming matrix with suspended cells is in liquid form. Once the liquid comes into contact with the compounds present in the testing region, a gel matrix is produced, trapping the suspended cells.

DETAILED DESCRIPTION OF THE INVENTION

The present invention is predicated in part on the discovery that various cells or cell types may be identified and differentiated based on differential biochemical reactions observed in gelled media. The multiple test medium of the present invention permits presumptive and rapid microbiological screening of various specimens. In particular, this invention in the form of a kit, is suitable for the easy and rapid biochemical testing of various cells, including commonly isolated bacteria, as well as actinomycetes and fungi (i.e., yeasts and molds), in addition to mammnalian, insect, and plant cells. In particular, the present invention provides compositions and methods for the phenotypic analysis of cells.

Phenotypic Analysis

The Darwinian belief in a common ancestry of Earth's gene pool and the concept of evolution by gene duplication, mutation, and rearrangement are at the foundation of the new field of genomics, a field that has evolved rapidly in recent years by successfully utilizing microorganisms as models. In genomic analysis, genes whose function(s) and coded protein are known in one cell type are used as a basis for extrapolation when a similar coding sequence is found in another cell type.

Initially, the pace of genomic research was limited by DNA sequencing technology. However, with new techniques developed in recent years, the pace of genomic sequencing has greatly accelerated and the sequencing effort is no longer considered a rate limiting step. Although the complete sequence of the human genome (approx. 75,000 genes) is still several years away, great strides have been made in the sequencing of single-celled microorganisms, which have smaller genomes (approx. 470 genes in the bacterium *Mycoplasma genitalium* to approx. 12,000 genes in the protozoan *Oxytricha similis*). As of September, 1997, the complete genomic sequences of 12 microbes had been obtained (See, Pennisi, Science 277:1432–1434 [1997]), representing the three domains of cellular life: eubacteria (e.g., *Eschenichia coli,* and *Bacillus subtilis*), archaea (e.g., *Methanococcus jannaschii,* and *Methanobacterium thermoautotrophicum*), and eucarya (e.g., *Saccharomyces cerevisiae*). The annotation of genes corresponding to open reading frames (ORFs) relies heavily on microorganisms, especially *E. coli*. Often the extrapolation from DNA sequence to enzyme or regulatory function is based upon sequence data from the best studied microbes (e.g., *E. coli, B. subtilis,* and *S. cerevisiae*) or from heterologous sequences that are cloned into *E. coli*. Yet even with a great deal of extrapolation, the percentage of genes with an "ascribed function" ranges from only 44% to 69%. There is a tremendous amount of functional information that remains to be determined and understood. Indeed, genome sequencing has reached a turning point, as indicated by Smith et al., "The next important challenge is to determine, in an efficient and reliable way, something about the function of each gene in the genomes" (Smith et al., Science 274:2069–2074 [1997]).

Over the past three decades, biologists have sought tools that would allow them to understand the workings of cells by analyzing all of the cell's genes simultaneously. The first breakthrough in this endeavor of "global analysis" came in the early 1970's with the introduction of one dimensional protein electrophoresis, which allowed scientists to separate and observe nearly all of a cell's proteins. This innovation was soon followed by the superior resolution obtained by two dimensional separations. One dimensional methods were next developed for DNA and mRNA analysis (i.e., Southern and Northern blot analysis).

Nucleic acid microarrays (See e.g., DeRisi et al., Science 278:680–686 [1997]) and gene fusion arrays (See e.g., Glaser, Genet. Enginer. News, Sep. 15, 1997, at pages 1 and 15), have been developed which can analyze the genotype and gene expression levels of cells.

By determining the function of genes, the analysis can go a step further, through the ascertainment of groups of genes which are regulated similarly and which, by implication, are likely to provide related functions in the cell. Though clearly of great value, these technologies still do not indicate the function of the gene, nor do they describe the phenotypic changes that occur in the cell of interest due to the presence of different alleles of that gene. The present invention solves these problems, by providing methods and compositions to assay the function of genes directly in cells. Unlike previous methods and compositions, the present invention permits the analysis of thousands of cell phenotypes simultaneously. This cellular approach is nicely complementary to the molecular techniques; it is contemplated that those skilled in the art will utilize the present invention in conjunction with molecular methods to characterize a wide variety of cell types.

Phenotypic Analysis of Yeast

As indicated above, the present invention is intended for use with eukaryotic, as well as prokaryotic cells. Indeed, the ease of finding phenotypic changes has also been demonstrated recently in yeast. As of 1996, of the 6000 genes in the chromosome of *S. cerevisiae,* less than one half had been known, and 30% could not be assigned a function (Goffeau et al., Science 274:546–567 [1996]). Subsequently, Smith and coworkers developed a method that allowed the introduction of Ty1insertion mutations into 97% of the genes on chromosome V. Testing this collection with only seven phenotypic tests based on the growth rate of the organism on certain media, they found detectable changes in 61.6% of the mutant strains (Smith et al., Science 274:2069–2074 [1996]). Moreover, these authors observed that disruption of many genes resulted in multiple phenotypes, and in fact uncovered previously undetected phenotypes for previously described genes, some of which were quite unexpected. In contrast, the present invention provides a much larger number, as well as more narrow phenotypic tests that provide much more detailed information about the change(s) in cell physiology that are detected in the yeast cells.

Summary of the Methods

The present invention provides useful, practical, efficient and cost-effective systems, including in one embodiment, an instrument which is used in conjunction with disposable testing panels, to allow the direct and simultaneous analysis of cells and cell lines for thousands of phenotypes. The present invention provides methods and compositions for the phenotypic analysis of prokaryotic, as well as eukaryotic cells. Indeed, the present invention is not limited to any particular organism, cell, or testing format.

In many embodiments, the present invention provides one or more testing panels, with each test panel including substrates for 95 phenotypic tests. In one embodiment, the substrates in the test panel include various carbon sources, while in other embodiments, the test panels include nitrogen, sulfur, phosphorus, and/or other substrates. Thus, it is intended that the present invention encompass testing panels with test substrates of any type suitable for the phenotypic testing of various cells.

In one preferred method, the present invention encompasses methods and compositions for the phenotypic testing of *E. coli*, which is an important "model" organism for many biochemical systems. In another embodiment, the present invention provides methods and compositions for the testing of isogenic strains with known mutations, in order to identify and characterize unexpected and/or misleading phenotypes.

In other preferred embodiments, the present invention provides methods and compositions to determine the function of genes of interest. For example, the present invention provides means to analyze and compare source strains and daughter strains for their phenotypic differences. Thus, in one embodiment, the gene of interest, with an unknown function in the source strain, is completely or partially inactivated by creating an altered allele in an isogenic daughter strain. Then, the source strain and the daughter strains are cultured simultaneously under identical conditions and tested in the testing panels described above in order to determine the phenotypic consequences of the alteration of gene function.

In other embodiments, a third cell strain is created. This third strain is a revertant of the mutation, derived from the daughter strain. It is intended that this approach will find use in situations in which the cells contain mutations that strongly select for secondary suppressor mutations in the cell line that otherwise can easily go unnoticed. By analyzing a revertant along with the source and daughter strains, one can tell whether any and all phenotypic differences between source and daughter are due to the original mutation or to second site mutations.

In still other embodiments, a gene of interest from another cell type is sequenced and its homolog is mutated in *E. coli* and/or *S. cerevisiae*. In yet other embodiments, a gene of interest from another cell type is cloned and expressed at a physiologically appropriate level in *E. coli* and/or *S. cerevisiae*. In addition, the present invention provides methods and compositions for the direct phenotypic analysis of cells which have been mutated. The present invention further contemplates knocking out expression of genes transiently with antisense RNA, and performing phenotypic analysis on cells with a transiently inactivated gene.

One limitation of the current phenotypic testing methods is the range of phenotypic tests covered, which is currently limited to carbon source oxidation tests. In contrast, the present invention provides methods and compositions for the analysis of thousands of phenotypic characteristics. For example, in some embodiments, one or more sets of 95 tests will be aimed toward each of the following groups of tests, which encompasses the majority of the catabolic functions of cells, as well as the majority of the biosynthetic functions of cells, and much of the macromolecular machinery of the cell including the ribosome, DNA and RNA polymerases, cellular respiration, transport and detoxification systems, cell wall, and inner and outer membranes: (1) carbon source oxidation tests (including peptide substrates), (2) carbon source fermentation tests, (3) amino and/or carboxy peptidase tests, (4) nitrogen source tests, (5) phosphorus source tests, (6) sulfur source tests, (7) auxotrophic tests for all essential metabolites such as amino acids, vitamins, polyamines, fatty acids, and/or nucleosides; (8) sensitivity tests for antibiotics and antimicrobials; (9) sensitivity tests for amino acid analogs, sugar analogs, nucleoside and base analogs, and/or mutagens, (10) sensitivity tests for dyes, detergents, heavy metals, oxidizing and/or reducing agents, and (11) other tests of general physiological interest such as growth at different pH concentrations, salt concentrations, utilization of different osmotic balancers, and/or ability to traverse various diauxic "shift-downs." The general issues in designing each group of tests are discussed below.

In addition to the carbon sources in such commercially available testing panels as the ES MicroPlate™, it is contemplated that any number of additional carbon sources of interest will be included in the present invention. For example, it is contemplated that peptides be included as carbon sources, as during the development of the present invention, it was observed that these carbon sources can provide very useful phenotypic tests. For example, it has been determined that *E. coli* can use D- and L-alanine, D- and L-serine, D- and L-threonine, D- and L-aspartate, L-asparagine, L-glutamine, L-glutamate, and L-proline as carbon sources. It is further contemplated that various chromogenic amino and carboxypeptidase substrates be used in the present invention.

Carbon source fermentation tests measure acid production from a variety of sugars, and therefore they can provide phenotypic information that is different from carbon source oxidation tests. These tests are performed using a chromogenic pH indicator, including, but not limited to such compounds as bromthymol blue, bromcresol purple, and neutral red.

The present invention also provides methods and compositions to observe utilization of nitrogen, phosphorus, and/or sulfur sources, using an indicator system (e.g., tetrazolium reduction) to demonstrate substrate utilization. Various nitrogen sources are contemplated for use in the present invention, including, but not limited to D-alanine, L-alanine, L-arginine, D-asparagine, L-asparagine, D-aspartic acid, L-aspartic acid, L-cysteine, L-cystine, D-glutamic acid, L-glutamic acid, L-glutamine, glycine, L-histidine, L-homoserine, D,L-B-hydroxy-glutamic acid, L-isoleucine, L- leucine, L-phenylalanine, L-proline, D-serine, L-serine, L-tryptophan, L-tyrosine, glutathione (as well as any peptide containing the above amino acids), adenosine, deoxyadenosine, cytosine, cytidine, deoxycytidine, D-glucosamine, D-galactosamine, D-mannosamine, N-acetyl-D-glucosamine, N-acetyl-D-galactosamine, N-acetyl-D- mannosamine, methylamine, ethylamine, butylamine, isobutylamine, amylamine, ethanolamine, ethylenediamine, pentamethylenediamine, hexamethylenetriamine, phenylethylamine, histamine, piperidine, pyrrole, B-alanine, glycocol, acetylglycocol, phenylglycine-o-carbonic acid, hippuric acid, urocanic acid, a-aminovaleric acid, γ-aminovaleric acid, α-arninoisovaleric acid, γ-aminoisovaleric acid, α-aminocaproic acid, γ-aminocaprylic acid, acetamide, lactamide, glucuronamide, formamide, propionamide, methoxylamine, thio-acetamide, cyanate, urea, diethylurea, tetraethylurea, biuret, parabanic acid, alloxan, alloxantine, allantoin, uric acid, theobromine, guanine, and xanthine. Example 18 provides a description of experiments conducted using various nitrogen sources.

Various phosphorous sources are contemplated for use in the present invention, including, but not limited to pyrophosphate, trimetaphosphate, 2'-mononucleotides, 3'-mononucleotides, 5'-mononucleotides, 2',3'-cyclic nucleotides, 3',5'-cyclic nucleotides, aryl-phosphates (e.g., p-nitrophenyl phosphate), phosphonates (e.g., aminoethyl phosphonate), sugar phosphates (e.g., glucose-1-phosphate), acid phosphates (e.g., 2-phospho-glyceric acid), aldehyde phosphates (e.g., glyceraldehyde-3 phosphate), α-glycerol phosphate, β-glycerol phosphate, inositol phosphates (e.g., phytic acid), phosphite, hypophosphite, and thiophosphate. Example 18 provides a description of experiments conducted using various phosphorous sources.

Various sulfur sources are contemplated for use in the present invention, including, but not limited to sulfur, thiosulfate, thiophosphate, metabisulfite, dithionite, tetrathionate, polysufide, cysteine, cystine, cysteic acid, cysteamine, cysteine sulphinic acid, cystathionine, lanthionine, ethionine, methionine, N-acetyl-methionine, N-acetyl-cysteine, glycyl-methionine, glycyl-cysteine, glutathione, L-djenkolic acid, L-2-thiohistidine, S-methyl-cysteine, S-ethyl-cysteine, methionine sulfoxide, methionine sulfone, taurine, thiourea, and thioglycolate. Example 18 provides a description of experiments conducted using various sulfur sources.

In addition, various amino and carboxy peptidases are contemplated for use in the present invention, including, but not limited to dipeptides containing all natural L-amino acids on the amino terminal, and all natural L-amino acids on the carboxy terminal, as well as suitable non-protein occurring amino acids, such as pyroglutamate, ornithine, α-amino butyrate, D-amino acids, etc.

The present invention also provides methods and compositions for autotrophicus testing using a minimal medium supplemented with various single nutrients. In one embodiment, the growth in the well where the organism is capable of using the nutrient results in a color change via tetrazolium reduction. Thus, mutations that result in auxotrophy cause the strain to fail to grow in all wells except the one containing the necessary nutrient. In some cases, the wells contain more than one nutrient, in order to allow analysis of genes that affect more than one biosynthetic pathways (e.g., isoleucine+valine (ilv), arginine+uracil (car), and purine+pyrimidine+histidine+tryptophan+nicotinamide (prs)). Various compounds are contemplated for use in this embodiment of the present invention, including, but not limited to L-amino acids, D-glutamic acid, D-aspartic acid, D-alanine, vitamins, nucleosides, polyamines, and fatty acids. In an alternative embodiment, a "drop out" medium or substrate is used. In this system, a complex defined supplement is used and one nutrient is missing in the substrate dispensed in each well (i.e., the medium lacks one nutrient of the substrate complex). Example 18 provides a description of experiments conducted to determine the autotrophicus requirements of an organism.

It is contemplated that for some embodiments of the present invention for sensitivity testing, a minimal medium is used, while in other cases, an enriched, defined medium is preferable. Furthermore, it is not intended that the present invention be limited to any particular testing substrates, as it is contemplated that any testing substrate suitable for use with the present invention will be utilized. In addition, as in other reactions, in one embodiment, growth in the wells can result in a color change via tetrazolium reduction. For each toxic agent, the optimal concentration for use in testing for sensitivity/resistance is determined for the cell type to be tested. Various sensitivity tests are contemplated, including tests utilizing compounds including, but not limited to oxidizing agents, reducing agents, mutagens, antibiotics, amino acid analogs, sugar analogs, nucleoside and base analogs, dyes, detergents, toxic metals, and toxic organics.

The present invention also provides methods and compositions for testing growth at extremes of pH and salt, and the compensatory effect of several compatible solutes. In addition, diauxic testing is performed with a limiting amount of a favored nutrient present in a well. In this embodiment, the cells need to adapt from a more favored to a less favored nutrient, and the lag and growth kinetics for numerous substrates can be measured quickly and efficiently in a microplate format.

It is also contemplated that the present invention be used with various gelling agents, including, but not limited to agar, pectin, carrageenan, alginate, alginic acid, silica, gellans and gum. In one embodiment, the pectin medium of Roth (U.S. Pat. Nos. 4,241,186, and 4,282,317; herein incorporated by reference) is used. However, this is not a preferred embodiment, as pectin is not a colorless compound itself. In one particularly preferred embodiment, the gellan of Kang et al. (U.S. Pat. Nos. 4,326,052 and 4,326,053, herein incorporated by reference) is used. In another preferred embodiment, carrageenan is used as the gelling agent. In a particularly preferred embodiment, carrageenan type II or any carrageenan which contains predominantly the iota form of carrageenan is used. In each embodiment, the cells to be tested are mixed in a suspension comprising a gelling agent, and then inoculated into a well, compartment, or other receptacle, which contains the biochemical(s) to be tested, along with a gel-initiating agent such as various cations. Upon contact of the gelling agent with the gel-initiating agent (e.g., cations), the suspension solidifies to form a viscous colloid or gel, with the cells evenly distributed throughout.

Indicator Plates of the Present Invention

The present invention also contemplates a multitest indicator plate that is generally useful in the phenotypic characterization, as well as identification and antimicrobial sensitivity testing of microorganisms. This medium and method are particularly targeted toward some of the most economically important organisms, as well as species of clinical importance. It is not intended that the invention be limited to a particular genus, species nor group of organisms. Indeed, it is contemplated that any cell type (e.g., microorganisms, as well as plant, mammalian, and insect cells) will find use in the present invention.

The present invention contemplates a testing device that is a microplate similar in structure to commonly used microtiter plates (i.e., "microplates" or "MicroPlates™") commonly used in the art and commercially available from numerous scientific supply sources (e.g., Biolog, Fisher, etc.). Thus, in one embodiment, standard 96-well microtiter plates (or "microplates") are used. In other embodiments, microtiter plates with more wells are used (e.g., 384 well and 1536 well microtiter plates or microplates). Furthermore, the microtiter plate (or microplate) format is suited for methods for kinetic analysis of substrate utilization by cells.

For example, in one embodiment, a test panel for detailed phenotypic testing of *E. coli* and *S. typhimurium* called the ES MicroPlate™ (Biolog) was used. This panel contains 95 carbon sources, which can be utilized by most strains of these species. To perform a test, identical cell suspensions of isogenic parental and mutant strains are prepared and pipetted into the 96 wells of a microtiter plate (e.g., a MicroPlate™). The cells are incubated for approximately 16–24 hours and if a substrate oxidation occurs in a given well, a violet/purple color is produced due to coupled reduction of a tetrazolium dye. Quantitation of the intensity of color is possible through use of a microplate reader or comparable instrument, or the plates can even be compared by eye. For observation of differences at a finer level, the MicroPlates™ can be read at frequent time intervals to determine the kinetics of color formation (i.e., carbon source oxidation rates) in each of the 96 wells. For a typical strain, perhaps 80 to 85 wells provide positive reactions and useful data.

An alternate embodiment of the invention generally relates to a "microcard" (i.e., such as the MicroCard™ developed by Biolog) device for the multiparameter testing of chemical, biochemical, immunological, biomedical, or microbiological samples in liquid or liquid suspension form in a small, closed, easy-to-fill device, and is particular suitable for multiparameter testing and identification of microorganisms. It is not intended that the present invention be limited to a particular sized device. Rather, this definition is intended to encompass any device smaller than the commonly used, 96-well microtiter plates. In one particularly preferred embodiment, the miniaturized cards (e.g., MicroCard™) is approximately 75 mm in width and 75 mm in length, and approximately 3 mm in depth. Approximately one-tenth the volume of cells are used to inoculate the compartments of the device, as compared to standard microtiter plates. Indeed, the present invention contemplates a device comprising: a) a housing; b) a testing region contained within the housing; c) a liquid receiving means on an external surface of the housing; d) a liquid flow-directing means providing liquid conunumication between the testing region and the liquid receiving means; and e) a gas-venting, liquid barrier in fluidic communication with the testing region.

After the device has been filled, a non-venting, sealing tape can be applied to the device to cover the gas-venting, liquid barrier to reduce the evaporation of the liquid from the device. In some embodiments, the tape can permit the molecular diffusion of oxygen and/or carbon dioxide into or out of the device to maintain the desired chemical or biochemical environment within the device for successful performance of the test. Where the liquid receiving means comprises liquid entry ports, a similar closing tape can be applied to close the port or ports to prevent spilling and evaporation of the liquid therefrom.

With any of the testing formats, the visual result that is detected by eye or by instrument can be any optically perceptible change such as a change in turbidity, a change in color, a change in fluorescence, or the emission of light, such as by chemiluminescence, bioluminescence, or by Stokes shift. Color indicators may be, but are not limited to, redox indicators (e.g., tetrazolium, resazurin, and/or redox purple), pH indicators, or various dyes and the like. Various dyes are described in U.S. Pat. Nos. 4,129,483, 4,235,964 and 5,134, 063 to Barry R. Bochner, hereby incorporated by reference. See also B. R. Bochner, Nature 339:157 (1989); and B. R. Bochner, ASM News 55:536 (1990). A generalized indicator useful for practice of the present invention is also described by Bochner and Savageau. See B. Bochner and M. Savageau, Appl. Environ. Microbiol., 33:434 (1977).

Testing based on the redox technology is extremely easy and convenient to perform. A cell suspension is prepared and introduced into the testing compartments of the device. Each compartment is prefilled with a different substrate.

In a preferred embodiment, all wells are prefilled with test formula comprising a basal medium that provides nutrients for the cells, a color-change indicator, as well as testing substrate(s) in sufficient concentration to trigger a color response when the testing substrate is utilieed by the cell suspension upon inoculation into the wells for testing (i.e., each well contains either the same or a different testing substrate). In a particularly preferred embodiment, redox purple is used as a redox indicator in the present invention.

One of the principal uses of the present invention is as a method and device for simple testing and speciation of microorganisms. The present invention contemplates microbiological testing based on the redox technology discussed above wherein a sample of a pure culture of microorganism is removed from a culture medium on which it has been grown and suspended at a desired density in saline, water, gel, gelling agent, buffer, or solution (e.g., PPS) . This suspension is then introduced into the compartments of the testing device which have been prefilled with basal medium, indicator, and substrate chemicals. The method is extremely easy and convenient to perform, and, unlike other approaches, the method and device do not require skilled personnel and cumbersome equipment.

In other preferred embodiments, the present invention involves the use of instruments such as the Biolog MicroStation™, an instrument system that allows the reading of testing panels inoculated with cells, and analyzes the data obtained from the testing panels. This allows the rapid analysis of multiple phenotypic characteristics for many cell types (e.g., microbial strains) in a short time.

Definitions

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and nondisposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "culture" refers to any sample or specimen which is suspected of containing one or more microorganisms or cells. In particularly preferred embodiments, the term is used in reference to bacteria and fungi. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fungi.

As used herein, the term "spore" refers to any form of reproductive elements produced asexually (e.g., conidia) or sexually by such organisms as bacteria, fungi, algae, protozoa, etc. It is also used in reference to structures within microorganisms such as members of the genus Bacillus, which provide advantages to the individual cells in terms of survival under harsh environmental conditions. It is not intended that the term be limited to any particular type or location of spores, such as "endospores" or "exospores." Rather, the term is used in the very broadest sense.

As used herein, the terms "microbiological media" and "microbiological culture media," and "media" refer to any substrate for the growth and reproduction of microorganisms. "Media" may be used in reference to solid plated media which support the growth of microorganisms. Also included within this definition are semi-solid and liquid microbial growth systems including those that incorporate living host organisms, as well as any type of media As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "basal medium," refers to a medium which provides nutrients for the microorganisms or cells, but does not contain sufficient concentrations of carbon compounds to trigger a color response from the indicator.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal, plant or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two hcell types together. Commonly used hybridomas include those created by the fusion of antibody-secreting B cells from an immunized animal, with a malignant myeloma cell line capable of indefinite growth in vitro. These cells are commonly cloned and used to prepare monoclonal antibodies.

As used herein, the term "mixed cell culture," refers to a mixture of two types of cells. In some embodiments, the cells are cell lines that are not genetically engineered, while in other preferred embodiments the cells are genetically engineered cell lines.

As used herein, the terms "monolayer," "monolayer culture," and "monolayer cell culture," refer to cells that have adhered to a substrate and grow in as a layer that is one cell in thickness. Monolayers may be grown in any format, including but not limited to flasks, tubes, coverslips (e.g., shell vials), roller bottles, etc. Cells may also be grown attached to microcarriers, including but not limited to beads.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the term "carbon source" is used in reference to any compound which may be utilized as a source of carbon for bacterial growth and/or metabolism. Carbon sources may be in various forms, including, but not limited to polymers, carbohydrates, acids, alcohols, aldehydes, ketones, amino acids, and peptides.

As used herein, the term "nitrogen source" is used in reference to any compound which may be utilized as a source of nitrogen for bacterial growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "sulfur source" is used in reference to any compound which may be utilized as a source of sulfur for bacterial growth and/or metabolism. As with carbon and nitrogen sources, sulfur sources may be in various forms, such as free sulfur, as well as compounds which contain sulfur.

As used herein, the term "phosphorus source" is used in reference to any compound which may be utilized as a source of phosphorus for bacterial growth and/or metabolism, As with carbon, nitrogen, and sulfur sources, phosphorus sources may be in various forms, such as free phosphorus, as well as compounds which contain phosphorus.

As used herein, the term "auxotroph" is used in reference to an organism that can be grown only in the presence of nutritional supplements (e.g. growth factors). Thus, in autotrophicus testing, auxotrophs will only grow in the presence of the supplement(s) that is/are necessary for their growth, and will not grow in media that lack the necessary supplement(s).

As used herein, the term "antimicrobial" is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the term "testing substrate" is used in reference to any nutrient source (e.g., carbon, nitrogen, sulfur, phosphorus sources) that may be utilized to differentiate bacteria based on biochemical characteristics. For example, one bacterial species may utilize one testing substrate that is not utilized by another species. This utilization may then be used to differentiate between these two species. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

Following exposure to a testing substrate such as a carbon or nitrogen source (or any other nutrient source), or an antimicrobial, the response of an organism may be detected. This detection may be visual (i.e., by eye) or accomplished with the assistance of machine(s) (e.g., the Biolog MicroStation Reader™). For example, the response of organisms to carbon sources may be detected as turbidity in the suspension due to the utilization of the testing substrate by the organisms. Likewise, growth can be used as an indicator that an organism is not inhibited by certain antimicrobials. In one embodiment, color is used to indicate the presence or absence of organism growth/metabolism.

As used herein, the terms "chromogenic compound" and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator" and "oxidation-reduction indicator" encompass all compounds commonly used for detection of oxidation/reduction potentials (i.e., "eH") including, but not limited to various types or forms of tetrazolium, resazurin, methylene blue, and quinone-imide redox dyes including the compounds known as "methyl purple" and derivatives of methyl purple. The quinone-imide redox dye known as methyl purple is referred to herein as "redox purple." In a particularly preferred embodiment, "redox purple" comprises the compound with the chemical structure shown in FIG. 5, VI. It is contemplated that analogous derivatives of the reagent (e.g., alkali salts, alkyl O-esters), with modified properties (e.g., solubility, cell permeability, toxicity, and/or modified color(s)/absorption wavelengths) will be produced using slight modifications of the methods described in Example 12. It is also contemplated that various forms of redox purple (e.g., salts, etc.), may be effectively used in combination as a redox indicator in the present invention.

As used herein, the terms "testing means" and "testing device" are used in reference to testing systems in which at least one organism is tested for at least one characteristic, such as utilization of a particular carbon source, nitrogen source, or chromogenic substrate, and/or susceptibility to an antimicrobial agent. This definition is intended to encompass any suitable means to contain a reaction mixture, suspension, or test. It is intended that the term encompass microplates, petri plates, microcard devices, or any other supporting structure that is suitable for use. For example, a microplate having at least one gel-initiating agent included in each of a plurality of wells or compartments, comprises a testing means. Other examples of testing means include microplates without gel-initiating means included in the well. It is also intended that other compounds such as carbon sources or antimicrobials will be included within the compartments. The definition encompasses the MicroPlate™ microtiter plates for characterization of microorganisms (available from Biolog). The definition is also intended to encompass a "microcard" or miniaturized plates or cards which are similar in function, but much smaller than standard microtiter plates (for example, many testing devices can be conveniently held in a user's hand). In particularly preferred embodiments, the microcards are the MicroCardm device described in U.S. Pat. Nos. 5,589,350, and 5,800,785, both of which are herein incorporated by reference (available from Biolog). It is not intended that the present invention be limited to a particular size or configuration of testing device or testing means. For example, it is contemplated that various formats will be used with the present invention, including, but not limited to microtiter plates (including but not limited to MicroPlates™), miniaturized testing plates (e.g., MicroCard™ miniaturized testing cards), petri plates, petri plates with internal dividers used to separate different media placed within the plate, test tubes, as well as many other formats.

As used herein, the term "gelling agent" is used in a broad generic sense, and includes compounds that are obtained from natural sources, as well as those that are prepared synthetically. As used herein, the term refers to any substance which becomes at least partially solidified when certain conditions are met. For example, one gelling agent encompassed within this definition is Gelrite™, a gellan which forms a gel upon exposure to divalent cations (e.g., $Mg^{2+}$ or $Ca^{2+}$); Gelrite™ is a gellan gum, produced by deacetylating a natural polysaccharide produced by *Pseudomonas elodea,* and is described by Kang et al. (U.S. Pat. Nos. 4,326,052 and 4,326,053, herein incorporated by reference).

Included within the definition are various gelling agents obtained from natural sources, including protein-based as well as carbohydrate-based gelling agents. One example is bacteriological agar, a polysaccharide complex extracted from kelp. Also included within the definition are such compounds as gelatins (e.g., water-soluble mixtures of high molecular weight proteins obtained from collagen), pectin (e.g., polysaccharides obtained from plants), carrageenans and alginic acids (e.g., polysaccharides obtained from seaweed), and gums (e.g., mucilaginous excretions from some plants and bacteria). It is contemplated that various carrageenan preparations will be used in the present invention, with iota carrageenan comprising a preferred embodiment. It is also contemplated that gelling agents used in the present invention may be obtained commercially from a supply company, such as Difco, BBL, Oxoid, Marcor, Sigma, or any other source.

It is not intended that the term "gelling agent" be limited to compounds which result in the formation of a hard gel substance. A spectrum is contemplated, ranging from merely a more thickened or viscous colloidal suspension to one that is a firm gel. It is also not intended that the present invention be limited to the time it takes for the suspension to gel.

Importantly, it is intended that the present invention provides a gelling agent suitable for production of a matrix in which organisms may grow (i.e., a "gel matrix"). The gel matrix of the present invention is a colloidal-type suspension of organisms produced when organisms are mixed with an aqueous solution containing a gelling agent, and this suspension is exposed to a gel-initiating agent. It is intended that this colloidal-type gel suspension be a continuous matrix medium throughout which organisms may be evenly dispersed without settling out of the matrix due to the influence of gravity. The gel matrix must support the growth of organisms within, under, and on top of the gel suspension.

As used herein the term "gel-initiating agent" refers to any compound or element which results in the formation of a gel matrix, following exposure of a gelling agent to certain conditions or reagents. It is intended that "gel-initiating agent" encompass such reagents as cations (e.g., $Ca^{2+}$, $Mg^{2+}$, and $K^+$). Until the gelling agent contacts at least one gel-initiating agent, any suspension containing the gelling agent remains "ungelled" (i.e., there is no thickening, increased viscosity, nor hardening of the suspension). After contact, the suspension will become more viscous and may or may not form a rigid gel (i.e., contact will produce "gelling").

As used herein, the term "inoculating suspension" or "inoculant" is used in reference to a suspension which may be inoculated with organisms to be tested. It is not intended that the term "inoculating suspension" be limited to a particular fluid or liquid substance. For example, inoculating suspensions may be comprised of water, saline, or an aqueous solution which includes at least one gelling agent. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "kit" is used in reference to a combination of reagents and other materials. It is contemplated that the kit may include reagents such as carbon sources, nitrogen sources, chromogenic substrates, antimicrobials, diluents and other aqueous solutions, as well as specialized microplates (e.g., GN, GP, ES, YT, SF-N, SF-P, and other MicroPlates™, obtained from Biolog), inoculants, miniaturized testing cards (e.g., MicroCards™), and plated agar media. The present invention contemplates other reagents useful for the growth, identification and/or determination of the antimicrobial susceptibility of microorganisms. For example, the kit may include reagents for detecting the growth of microorganisms following inoculation of kit components (e.g.,tetrazolium or resazurin included in some embodiments of the present invention). It is not intended that the term "kit" be limited to a particular combination of reagents and/or other materials. Further, in contrast to methods and kits which involve inoculating organisms on or into a preformed matrix such as an agar surface or broth, the present invention involves inoculation of a testing plate in which the organisms are suspended within a gel-forming matrix.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "defmitive diagnosis" is used to refer to a final diagnosis in which the etiologic agent of the patient's disease has been identified. The term "definitive identification" is used in reference to the final identification of an organism to the genus and/or species level.

Although embodiments have been described with some particularity, many modifications and variations of the preferred embodiment are possible without deviating from the invention.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); niol (nanomoles); g (grams); mg (milligrams); $\mu$g (micrograms); ng (nanograms); 1 or L (liters); ml (milliliters); $\mu$l (microliters); cm (centimeters); mm (millimeters); $\mu$m (micrometers); nm (nanometers); °C. (degrees Centigrade); TSA (trypticase soy agar); YME or YEME (Yeast extract-malt extract agar); EMB (eosin methylene blue medium); MacConkey (MacConkey medium); Redigel (RCR Scientific, Goshen, Ind.); Gelrite™ (Merck and Co., Rahway, N.J.); Remel, (Remel, Lenexa, Kans.); Oxoid (Oxoid, Basingstoke, England); BBL (Becton Dickinson Microbiology Systems, Cockeysville, Md.); DIFCO (Difco Laboratories, Detroit, Mich., now part of Becton-Dickinson); Acumedia (Acumedia, Baltimore, MD); U.S. Biochemical (U.S. Biochemical Corp., Cleveland, Ohio); Fisher (Fisher Scientific, Pittsburgh, Pa.); Sigma (Sigma Chemical Co., St. Louis, Mo.); Biolog (Biolog, Inc., Hayward, Calif.); ATCC (American Type Culture Collection, Rockville, Md.); CBS (Centraalbureau Voor Schimmelcultures, Delft, Netherlands); CCUG (Culture Collection of University of Gothenberg, Gothenberg, Sweden); GSU (Georgia State University, Atlanta, Ga.); NRRL (USDA Northern Regional Research Laboratory, Peoria, Ill.); and NCYC (National Collection of Yeast Cultures, Norwich, England); NCCLS (National Conmmittee for Clinical Laboratory Standards); API (API Analytab Products, Plainview, N.Y.); Flow (Flow Laboratories, McLean, Va.); bioMerieux (bioMerieux, Hazelwood, Mo.); and Molecular Devices (Molecular Devices, Mountain View, Calif.). The three-letter abbreviations conventionally used for amino acids (e.g., "ala" designates alanine or an alanine residue) are also used in some of the following Examples.

The following Tables list the principal bacterial strains used in the following Examples, with Table 2 listing the various actinomycetes, and Table 3 listing other species of microorganisms.

TABLE 2

Actinomycetes Tested

| Organism | Source and Number |
| --- | --- |
| Actinomadura ferruginea | USDA NRRL B-16096 |
| Actinoplanes rectilineatus | USDA NRRL B-16090 |
| Micromonospora chalcea | USDA NRRL B-2344 |
| Norcardiopsis dassonvillei | USDA NRRL B-5397 |
| Saccharopolyspora hirsuta | USDA NRRL B-5792 |
| Streptomyces albidoflavus | USDA NRRL B-1271 |
| Streptomyces coeruleoribidus | USDA NRRL B-2569 |
| Streptomyces griseus | USDA NRRL B-2682 |
| Streptomyces hygroscopicus | USDA NRRL B-1477 |
| Streptomyces lavendulae | USDA NRRL B-1230 |
| Streptoverticillium salmonis | USDA NRRL B-1484 |

TABLE 3

Other Organisms Tested

| Organism | Source and Number |
| --- | --- |
| Escherichia coli | ATCC #25922 |
| Staphylococcus aureus | ATCC #29213 |
| Providencia stuartii | ATCC #33672 |
| Pseudomonas cepacia | ATCC #25416 |
| Neisseria lactamica | CCUG #796 |
| Xanthomonas maltophilia | ATCC #13637 |
| Vibrio metschnikovii | ATCC #7708 |
| Cedecea neteri | ATCC #18763 |
| Rhodococcus equi | ATCC #6939 |
| Dipodascus ovetensis | ATCC #10678 |
| Cyptococcus laurentii | CBS #139 |
| Cryptococcus terreus A | CBS #1895 |
| Kluyveromyces marxianus | GSU #C90006070 |
| Saccharomyces cerevisiae A | NCYC ##505 |
| Williopsis saturnus var. saturnus | GSU #WC-37 |
| Penicillium notatum | ATCC #9179 |
| Penicillium chrysogenum | ATCC #11710 |
| Rhizomucor pusillus | ATCC #32627 |
| Aspergillus niger | ATCC #16404 |
| Tricophyton mentagrophytes | ATCC #9129 |

EXAMPLE 1

Primary Growth of Actinomycetes

In this example, several attempts were made to grow various actinomycetes in R2A liquid media prepared from the recipe of Reasoner and Geldreich (Reasoner and Geldreich, Appl. Environ. Microbiol., 49:1–7 [1985]), prior to preparation of inoculum suspensions for inoculating commercially available MicroPlates™ from Biolog (e.g., Biolog's GN, GP, and YT MicroPlates™). This method proved unsuccessful and cumbersome. Also, it was virtually impossible to obtain uniform (homogenous) cultures of satisfactory quality.

Next, these organisms were grown on the surface of various agar media. It was thought this might provide a very simple means to harvest spores from the culture, as the colonies tend to anchor into the agar matrix itself. The media used in this example included Sporulation Agar (described by R Atlas in *Handbook of Microbiological Media*, CRC Press, Boca Raton, Fla., p. 834 [1993]), and YEME Agar with glucose omitted (described by E. B. Shirling and D. Gottlieb, in "Methods for Characterization of Streptomyces Species," Int'l J. System. Bacteriol., 16:313–330 [1966]) (hereinafter referred to as YEMEWG).

Sporulation Agar (also known as m-Sporulation Agar) comprises agar (15 g/l), glucose (10 g/l), tryptose (2 g/l), yeast extract (1 g/l), beef extract (1 g/l), and $FeSO_4.7H_2O$ (1 µg/l), pH 7.2±0.2 at 25° C. These ingredients are added to 1 liter of distilled/deionized water, and mixed thoroughly with heat to boiling. After the mixture has dissolved, it is autoclaved at 15 psi (121° C.) for 15 minutes, and dispensed into plates.

YEMNEWG Agar comprises Bacto yeast extract (4 g/l; Difco), and Bacto-malt extract (10 g/l; Difco). These ingredients are added to 1 liter of distilled/deionized water and mixed thoroughly. The pH is adjusted to 7.3, and agar (20 g/l) is added to the mixture. The mixture is then autoclaved at 121° C. for 15–20 minutes, and dispensed into Petri plates after it is sufficiently cooled. YEMEWG was used because preliminary studies indicated that, while glucose-containing YEME agar was adequate for growth of the Streptomyces species, genera such as Nocardiopsis and Actinoplanes grew better when glucose was omitted from the medium recipe.

Because of the interest in obtaining spores, media that encourage sporulation were tried. For example, YEMEWG was found to be particularly useful, as this medium gave satisfactory growth and sporulation of most strains tested within 2–4 days of incubation at 26° C. Various agar concentrations were tested during these preliminary studies, and it was further observed that when YEMEWG was used, improved sporulation occurred in the presence of a higher agar concentration (e.g., 25 g/l, rather than the 15 g/l, traditionally used in microbiological agar media).

This approach of growing actinomycetes on a sporulation-inducing medium would have the additional benefit of standardizing the physiological state of the organisms, and would permit preparation of inocula primarily from spheroidal spores. It was usually a relatively simple matter to produce uniform, homogeneous suspensions containing spores. Occasionally, however, large clumps of the organisms and their aerial mycelia are obtained which do not readily disperse in solution. When clumps are formed, the suspension is allowed to sit for a few minutes, permitting the large fragments to settle to the bottom of the tube. Use of a light inoculum (i.e., a 1:10 dilution of an initial suspension where the initial suspension has a transmittance level of 70%) also helps avoid problems with clumping of large fragments. Therefore, clumps can be avoided in the preparation of the final inoculum because only a small, clump-free aliquot of the initial suspension is used. For those organisms that sporulate poorly, fragments of rods and/or mycelial filaments were obtained from the agar surface in the same manner.

This example highlights the advantages of the present invention for the primary growth and subsequent characterization of actinomycetes, in contrast to references that indicate growth of actinomycetes is very slow. For example, Bergey's Manual® (T. Cross, "Growth and Examination of Actinomycetes—Some Guidelines," in J. Holt et al., "The Actinomycetes," Bergey's Manual® of Determinative Bacteriology, 9th ed., Williams & Wilkins, Baltimore, pp. 605–609 [1994]) indicates that "mature aerial mycelium with spores may take 7–14 days to develop, and some very slow-growing strains may require up to 1 month's incubation." This is in stark contrast to the present invention, in which heavy growth and sporulation is achieved within 24 days of incubation.

EXAMPLE 2

Preparation of Inoculum

In this experiment, a method more optimal for preparation of a homogeneous inoculum was determined. For example, it was found that an easy and reproducible method was to grow the organisms as described in Example 1 on YEMEWG-prepared with 25 g/l agar, or other suitable agar medium. A low density inoculum (i.e., 0.01 to 0.1 $OD_{590}$) was then prepared by moistening a cotton swab and rubbing it across the top of the colonies to harvest mycelia and spores. It was determined that sterilized water and 0.85% sterile saline worked reasonably well as a suspension medium for all strains. However, some strains exhibited a preference for one or the other. For example, *Streptomyces coeruleoribidus, S. hygroscopicus,* and *S. albidoflavus* produced an average of ten additional positive reactions when water was used as the suspension medium, whereas thirteen additional positive reactions were observed for *S. lavendulae* when saline was used as the suspension medium. The majority of the Actinomycetes performed better when water was used. Therefore, water was used routinely to prepare the suspensions.

EXAMPLE 3

Preparation of Multi-Test Plates

The inocula prepared as described in Example 2 were used to inoculate various Biolog MicroPlates™, including the commercially available GN, GP, and YT MicroPlates™. A few strains worked well upon inoculation into the GN or GP MicroPlates™ (e.g., *S. lavendulae*). However, for most strains (e.g., *A. ferruginea,* and *N. dassonvillei*) no positive reactions were observed. In addition, positive reactions were observed in all of the test wells for some organisms (e.g., *S. hirsuta*), indicating that there was a problem with false positive results.

Much improved results were obtained when the wells located in the bottom five rows of the YT MicroPlate™ were used. It was thought that this observation was due to the absence of tetrazolium in these wells, as the tetrazolium present in the other wells appeared to inhibit the growth of the organisms. This was confirmed by testing the ability of the organisms to grow on YEMEWG agar media containing various concentrations of tetrazolium (20, 40, 60 and 80 mg/l). Many strains (e.g., *S. coeruleoribidus, S. hygroscopicus, S. lavendulae, M. chalcea, N. dassonvillei,* and *A. rectilineatus*) were inhibited at all of these tetrazolium concentrations. Other organisms, such as *S. griseus, S. albidoflavus,* and *S. hirsuta,* were somewhat inhibited at the higher tetrazolium concentrations, but grew in tetrazolium concentrations of 20 and 40 mg/l.

Based on these experiments, MicroPlates™ containing no tetrazolium (e.g., "SF-N" [GN MicroPlate™ without tetrazolium], and "SF-P" [GP MicroPlate™ without tetrazolium] MicroPlates™) were then tested. These plates were inoculated with water or saline suspensions of various actinomycetes, and incubated at 26° C. for 1–4 days. Increased turbidity (i.e., growth of the organisms) was readable visually, or with a microplate reader (e.g., a Biolog MicroStation Readers™, commercially available from Biolog), in as little as 24 hours for some strains. For the slow growing strains, growth was readable and the results interpretable within 3–4 days, representing a significant improvement over the 7–10 day incubation period required using routine methods.

EXAMPLE 4

Use Of Gelrite™

Although growth was observable in the multi-test system described in Example 3, the results were still not completely satisfactory, due to the unique growth characteristics of the actinomycetes. Many of these strains adhered to the plastic walls of the microplate wells, thereby making detection of increased turbidity less than optimal. When the inoculating suspension is a liquid, turbidity often was concentrated along the outer circumference of the wells, rather than producing a uniform dispersion of turbidity throughout the wells.

In order to facilitate uniform dispersion of the inoculating suspension containing organisms throughout the well, a gelling agent was added to the suspension to prevent individual cells from migrating to the well walls. For example, preparations of Gelrite™ (commercially available from Sigma, under this name, as well as "Phytagel") were found to be highly satisfactory. Gelrite™ does not form a gel matrix until it is exposed to gel-initiating agents, in particular, positively charged ions such as divalent cations (e.g., $Mg^{2+}$ and $Ca^{2+}$). As soon as the Gelrite™ comes into contact with the salts present in the bottom of the microplate wells, the gelling reaction begins and results in the formation of a gel matrix within a few seconds.

Various concentrations of Gelrite™ were tested, including 0.1, 0.2, 0.3, 0.4, 0.5 and 0.6%. All concentrations gelled in the microplate, with the higher concentrations producing a harder gel.

In view of the fact that most of the actinomycetes are obligate aerobes, there was a concern that the oxygen concentration within the gel must be sufficient to permit growth. Thus, various gel depths were tested by using 50, 100, or 150 μl suspensions of organisms in the wells. Each of these depths resulted in good growth of organisms, although it was observed that 0.4% Gelrite™ and an inoculum of 100 μl produced optimal results, even with organisms such as *Streptomyces lavendulae,* a species that is strongly hydrophobic and clings to the walls of wells when it is suspended in water. The 0.4% concentration of Gelrite™ was found to produce an appropriate degree of viscosity to readily permit preparation of microbial suspensions and still be easily pipetted.

The entire procedure for growth and testing of the actinomycetes required a total of 3–7 days, including primary inoculation on YEMEWG medium and other suitable media to determination and analysis of the final results. Importantly, a minimum amount of personnel time was required (i.e., just the few minutes necessary to inoculate the primary growth medium and then prepare the suspension for biochemical testing). Thus, the present invention provides a much improved means for the rapid and reliable identification of actinomycetes.

EXAMPLE 5

Comparison of Water and Gelrite™

In this Example, the eleven actinomycetes listed in Table 2 were tested in both water and gel suspensions. For each organism, a water suspension of organisms with an optical transmittance of 70%, was diluted 1:10 in either water or 0.4% Gelrite™. Thus, two samples of each organism were produced, one sample being a water suspension and one sample being a suspension which included Gelrite™.

One hundred microliters of each sample were inoculated into SF-P MicroPlates™ (GP MicroPlates™ without tetrazolium; commercially available from Biolog). The MicroPlates™ were incubated at 27° C. for 48 hours, and observed for growth. As shown in the table below, the number of positive reactions increased dramatically for the organisms suspended in Gelrite™, as compared to water.

TABLE 4

Growth of Selected Streptomyces Species

| | Number of Positive/Borderline Reactions in Water Suspensions (+/b) | Number of Positive/Borderline Reactions in Gel Suspensions (+/b) |
|---|---|---|
| Steptomyces coeruleorubidus | 5/35 | 35/25 |
| Streptomyces griseus | 30/15 | 43/12 |
| Streptomyces lavendulae | 8/18 | 24/12 |

EXAMPLE 6

Use of Resazurin

In this Example, three concentrations of resazurin dye (25 mg/l, 50 mg/l, and 75 mg/l) were used as a redox color indicator of organism growth and metabolism. All of the eleven actinomycete strains listed in Table 2 were tested using these three concentrations of resazurin, and 0.4% Gelrite™.

The expected color reaction, a change from blue to pink and eventually to colorless, as the dye is progressively reduced, occurred with all test organisms after 48 hours of incubation at 27° C. This observation provides a supplemental indicator of organism metabolism in addition to turbidity. No single resazurin concentration provided uniformly optimal results. For example, N. dassonvillei produced a good differential pattern of color change at 25 mg/l and 50 mg/l, whereas S. lavendulae produced false positive results (i.e., all colorless wells) at the lower concentrations (25 mg/l and 50 mg/l), but a good differential pattern of color change at 75 mg/l.

Although the resazurin concentration may need to be adjusted depending upon the organism tested, the use of resazurin as a color indicator may provide additional valuable information to characterize organisms at the species or strain level.

In the course of these experiments, it was also observed that pigments produced by some actinomycetes in the various carbon sources tended to create very distinct and unique patterns. The unexpected observation was made that pigment production was enhanced by using a gel-forming substance in the inoculant.

Thus, different color patterns were obtained with the differing resazurin dye concentrations in combination with the natural pigments produced. For example, at 50 mg/l resazurin, M. chalcea produced a range of color intensities from colorless to light pink to bright pink and purple. S. hygroscopicus produced a range of colors from yellow and orange, to colorless, pink and blue. Other species exhibited other distinct color patterns in the wells. This additional information related to pigmentation and resazurin dye reduction, may be valuable to taxonomists and others interested in characterizing specific strains and/or species of actinomycetes.

EXAMPLE 7

Use of Alternative Gelling Agents

Other gelling agents were tested in this Example. In addition to Gelrite™, alginic acid,. carrageenan type I, carrageenan type II, and pectin were tested for their suitability in the present invention. All of these compounds are commercially available from Sigma.

Of these compounds, pectin was found to be unsuitable when tested by adding 1% pectin to SF-P MicroPlates™. Pectin has a yellowish cast to it, and is therefore not a colorless or clear compound. Furthermore, gelling was dependent upon the presence of sugars in the microplate wells. Because many of the substrates tested in this multitest format do not contain sugars, gelling did not occur uniformly in all wells.

All of these gelling agents with the exception of pectin, were tested with the eleven actinomycetes listed in Table 2. The same MicroPlates™ (SF-P), incubation time and temperature, as described in Example 5 above, were used. The only variables were the different gelling agents and varying concentrations of these agents.

The optimal viscosity and performance for each gelling agent was determined. Optimal viscosity and performance was achieved at 1% alginic acid; 0.2% was optimum for both types of carrageenan; and 0.4% was optimum for Gelrite™. All of these gelling agents were also diluted to half the above concentrations and found to be useful even at these lower concentrations.

Overall, the results for Gelrite™ and carrageenan types I and II were similar, and the difference in gel concentration did not affect the results significantly. However, the results for alginic acid were not as clearcut when the MicroPlates™ were observed by eye, as compared to the use of an automatic plate reader (e.g., Biolog MicroStation Reader™, Biolog). Indeed, when read by eye, the results with alginic acid were somewhat inferior to those obtained with Gelrite™. Carrageenan type II was slightly better than type I and it was also comparable to or better than Gelrite™. Surprisingly, the carrageenan type II functions as effectively as the Gelrite™, although the carrageenan does not form a rigid gel. This indicates that it is not necessary that a rigid gel be formed in order for the beneficial effects of these colloidal gelling agents to be observed.

EXAMPLE 8

Testing of Other Bacterial Species

In addition to the actinomycetes, the present invention is also suitable for the rapid characterization of numerous and diverse organisms, such as those listed in Table 3. The gram-negative bacteria tested covered a range of genera and tribes, including Pseudomonas cepacia, Providencia stuartii, Neisseria lactamica, Xanthomonas maltophilia, Vibrio metschnikovii, Cedecea neteri, and Escherichia coli. Various gram-positive bacteria were also tested, including Rhodococcus equi and Staphylococcus aureus.

These organisms were tested basically as described in Example 5 above, with GN MicroPlates™ (Biolog) used to test the gram-negative organisms, and GP MicroPlates™ (Biolog) used to test the gram-positive organisms. In addition, ES MicroPlates™ (Biolog) were also tested with some of the gram-negative species. Inoculation in 0.4% Gelrite™ was compared to inoculation in 0.85% saline. The inoculation densities used were those normally recommended for these MicroPlate™ test kits (55% transmittance for the gram-negative organisms, and 40% for the gram-positive organisms). Following inoculation of the MicroPlates™ with 150 µl suspensions of organisms in either saline or Gelrite™ per well, the MicroPlates™ were incubated at 35° C. for 16–24 hours.

All of these organisms performed well in the gel, with most producing better results in gel than in saline. For example, in the ES MicroPlate™, *E. coli* produced 43 positive reactions within 24 hours when the gel was used, but only 36 positive reactions when saline was used. A correct identification of *C. neteri* was obtained after only 4 hours of incubation in the Gelrite™, whereas overnight incubation was required for saline. Thus, a correct identification of this organism is possible in a much shorter time period than the 24 hour incubation usually required for traditional testing methods.

In contrast to conventional biochemical testing materials and methods traditionally used, the present invention often achieves a definitive identification in a significantly shorter time period.

EXAMPLE 9

Testing of Eukaryotic Microorganisms—Yeasts

This experiment was designed to determine the suitability of the present invention for use in identification of eukaryotic microorganisms, such as yeasts. In this experiment, two types of reactions were observed to establish a metabolic pattern: a) assimilation reaction tests which are based on turbidity increases due to carbon utilization by the organisms; and b) oxidation tests, which also test for carbon utilization, but which detect utilization via a redox color change of the organism suspension.

In this experiment, yeasts were first grown on BUY Agar (Biolog) a solid agar medium, and harvested from the agar surface as described in Example 2 above. The organisms included in this example are listed in Table 3 (*D. ovetensis, C. laurentii, C. terreus, K. marxianus, S. cerevisiae,* and *W. saturnus*). Biolog YT MicroPlates™ (available commercially from Biolog) were then inoculated with an inoculum having an optical transmittance of 50%, in either water or 0.4% Gelrite™. Each well of the YT MicroPlate™ was inoculated with 100 µl of either the water or 0.4% Gelrite™ suspension of organisms. Thus, there were two sets of 6 MicroPlates™ each. The inoculated MicroPlates™ were incubated at 27° C., and the results observed at 24, 48, and 72 hours of incubation.

With the oxidation tests, in most cases, the color changes developed more rapidly in the plates with Gelrite™ used as the inoculant, compared to the plates with water as the inoculant. For example, *D. ovetensis, W. saturnus, K. marxianus,* and *C. laurentii* gave stronger reactions at 48 hours with Gelrite™. In contrast, *S. cerevisiae* and *C. terreus* gave stronger reactions at 48 hours with water.

With the assimilation tests, in all cases the Gelrite™ was superior or equivalent to the water inoculant. The data shown in the Tables below clearly demonstrate that more positive (+) and borderline (b) reactions were obtained overall, when Gelrite™ was used.

TABLE 5

Positive (+) and Borderline (b) Reactions After One Day of Incubation

| Organism | Water (+/b) | Geltrite ™ (+/b) |
|---|---|---|
| D. ovetensis | 0/5 | 17/7 |
| K. marxianus | 14/3 | 16/9 |
| W. saturnus | 9/7 | 40/9 |
| C. terreus A | 4/14 | 33/3 |
| C. laurentii | 61/5 | 67/8 |
| S. cerevisiae A | 24/5 | 22/2 |

TABLE 6

Positive (+) and Borderline (b) Reactions After Two Days of Incubation

| Organism | Water (+/b) | Gelrite ™ (+/b) |
|---|---|---|
| D. ovetensis | 9/2 | 22/2 |
| K. marxianus | 14/5 | 39/4 |
| W. saturnus | 23/7 | 46/5 |
| C. terreus A | 21/7 | 45/4 |
| C. laurentii | 65/0 | 77/3 |
| S. cerevisiae A | 24/6 | 24/0 |

TABLE 7

Positive (+) and Borderline (b) Reactions After Three Days of Incubation

| Organism | Water (+/b) | Gelrite ™ (+/b) |
|---|---|---|
| D. ovetensis | 21/9 | 23/7 |
| K. marxianus | 27/5 | 43/7 |
| W. saturnus | 48/6 | 52/3 |
| C. terreus A | 20/8 | 58/5 |
| C. laurentii | 68/6 | 78/5 |
| S. cerevisiae A | 24/8 | 24/2 |

In these experiments, the surprising observation was made that some organisms could be identified faster due to better growth (i.e., growth that appeared much more rapidly and at a greater density), in the plate with the Gelrite™, as compared to the plate with water. For example, *Dipodascus ovetensis* developed a metabolic reaction pattern sufficient for correct identification after 24 hours of incubation in the Gelrite™ plate, while 48 hours of incubation was required to make the proper identification in the water plate.

In addition, many of the limitations and deficiencies of currently commercially available yeast identification systems, such as the Minitek (BBL), API 20C (API), expanded Uni-Yeast-Tek System (Flow), and Vitek (Biomerieux) were overcome or avoided in the present example (see e.g., G. A. Land (ed.), "Mycology," in H. D. Isenberg (ed.), *Clinical Microbiology Procedures Handbook,* American Society for Microbiology, in particular "Commercial Yeast Identification Systems," pp. 6.10.1 through 6.10.5, [1994]). For example, in the Vitek system, heavily encapsulated yeasts and isolates with extensive mycelial growth are sometimes difficult to suspend. As indicated above, this limitation is avoided by the present invention, allowing for reliable and reproducible testing procedures and systems. In summary, the Gelrite™ was shown to be clearly superior to water for the rapid identification of eukaryotic microorganisms.

EXAMPLE 10

Testing of Eukaryotic Microorganisms—Molds

This experiment was designed to determine the suitability of the present invention for use in identification of eukaryotic microorganisms, such as molds.

In this experiment, the molds were first grown on modified Sabouraud-Dextrose agar (commercially available from various sources, including Difco). This medium is prepared by thoroughly mixing dextrose (20 g/l), agar (20 g/l), and neopeptone (1 g/l) in 1 liter of distilled/deionized water. Heat is applied, until the mixture boils. The medium is autolaved for 15 minutes at 15 psi (121° C.). After cooling, the medium is distributed into petri plates.

The organisms included in this example are listed in Table 3 (*P. notatum, P. chpysogenum, R. pusillus, A. niger* and *T. mentagrophytes*). After they were grown on Sabouraud-Glucose agar, an inoculum was prepared as described in Examnple 1. YT and SP-F MicroPlates™ (Biolog) were then inoculated with a 1:10 dilution of a starting inoculum having an optical transmittance of 70%, in water, 0.2% carrageenan type II, or 0.4% Gelrite™.

Each well of the SF-P MicroPlates™ was inoculated with 100 μl of organisms suspended in either water, 0.2% carrageenan type II, or 0.4% Gelrite™. For the YT plates, 100 μl of organisms suspended in either water, or 0.4% Gehrite™ were used to inoculate the wells. The inoculated MicroPlates™ were incubated at 25° C., and the results observed by eye and using a MicroStation Reader™ (Biolog) at 24 hour increments for a total of 4 days of incubation.

In nearly all cases, the turbidity changes developed more rapidly in the plates with carrageenan or Gelrite™ used as the inoculant, compared to the plates with water as the inoculant. The data shown in the Tables below clearly demonstrate that for most organisms, more positive (+) and borderline (b) reactions were obtained overall, when carrageenan or Gelrite™ was used, as compared to water. The results in these Tables are those observed with the MicroStation Reader™ (Biolog).

It was also observed that the improvement in the results using Gelrite™ or carrageenan as the gelling agent were sometimes more apparent when the test results were read visually, rather than by a machine (Biolog's MicroStation Reader™). This was the case with *T. mentagrophytes*, where the improved results obtained with carrageenan were in fact, also obtained with Gelrite™, although the reader did not detect this accurately at 72 hours. However, with longer incubation periods (e.g., 4–5 days), the visual and machine readings agree very well in nearly all cases.

TABLE 8

Positive (+)/Borderline (b) Reactions
After 72 Hours of Incubation in SF-P MicroPlates ™

| Organism | Carrageenan (+/b) | Gelrite ™ (+/b) | Water (+/b) |
|---|---|---|---|
| P. nolatum | 54/11 | 52/14 | 47/11 |
| P. chrysogenum | 56/13 | 54/11 | 50/17 |
| R. pusillus | 4/13 | 5/5 | 2/6 |
| A. niger | 23/17 | 29/12 | 17/10 |
| T. mentagrophytes | 16/12 | 3/6 | 5/1 |

TABLE 9

Positive (+)/Borderline (b) Reactions
After 72 Hours of Incubation in YT MicroPlates ™

| Organism | Gelrite ™ (+/b) | Water (+/b) |
|---|---|---|
| P. notatum | 78/5 | 67/4 |
| P. chrysogenum | 81/1 | 75/10 |
| R. pusillus | 17/22 | 13/26 |
| A. niger | 78/2 | 51/11 |
| T. mentagrophytes | 2/1 | 2/1 |

EXAMPLE 11

Antimicrobial Susceptibility Testing

In this Example, the suitability of a gel matrix for use in antimicrobial susceptibility testing was investigated. Two organisms, *Staphylococcus aureus* (ATCC #29213) and *Escherichia coli* (ATCC#25922) were tested against a panel of three antimicrobial agents: ampicillin, kanamycin, and tetracycline. All three antimicrobials were obtained from Sigma. Biolog's MT MicroPlates™ (Biolog), were used with 12.5 μl of a 10% glucose solution added to each well. Kanamycin and tetracycline were dissolved. in sterile water. Ampicillin was dissolved in phosphate buffer (pH 8.0)(0.1 M/l $NaH_2PO_4.H_2O$). For each antimicrobial agent, a dilution series ranging from 0.25 μg/ml to 32 μg/ml final concentration, was prepared. A 15 μl aliquot of each dilution was pipetted into the wells of the MicroPlates™, with water used to dilute the kanamycin and tetracycline, and phosphate buffer (pH 6.0)(0.1 M/l $NaH_2PO_4.H_2O$) used to dilute the ampicillin. For each MicroPlates™, a row of eight wells without antimicrobials was used as a control. In the MT MicroPlates™, tetrazolium is included as a color indicator. Unlike the actinomycetes, the most commonly isolated gram-negative and grain-positive bacteria are not significantly inhibited by the presence of tetrazolium in these MicroPlates™.

In addition to the MT MicroPlates™, Biolog's SF-N MicroPlates™ (GN MicroPlates™ without tetrazolium), and SF-P MicroPlates™ (GP MicroPlates™ without tetrazolium) were tested (all of these plates were obtained from Biolog). *E. coli* was inoculated into the SF-N MicroPlates™, and *S. aureus* was inoculated into the SF-P MicroPlates™. In these MicroPlates™, 25 mg/l of resazurin was added as a color indicator as an alternative to tetrazolium. In addition, 12.5 μl of 10% glucose solution and 15 μl of each antimicrobial dilution were added to each well, as described in the paragraph above.

All of the wells in all of the MicroPlates™ were inoculated with 100 μl of a very light suspension (e.g., a 1:100 dilution of a 55% transmittance suspension of *E. coli*, and a 1:100 dilution of a 40% transmittance suspension of *S. aureus*), and incubated overnight at 35° C.

For each organism and each MicroPlate™, 0.85% saline and 0.4% Gelrite™ were compared, by looking visually for the lowest antimicrobial concentration that inhibited dye (tetrazolium or resazurin) reduction. The minimum inhibitory concentration (SIC) for each organism was determined after 18 hours of incubation at 35° C. The MIC values for each organism, as determined from these experiments, are provided in the Tables below.

TABLE 10

MIC Determinations for *E. coli*
in MT MicroPlates ™ Containing Tetrazolium
and SF-N MicroPlates ™ Containing Resazurin

| | Antimicrobial | | |
|---|---|---|---|
| Diluent | Ampicillin | Kanamycin | Tetracycline |
| Saline | 1–2 | 16–32 | 0.5–1 |
| Gelrite ™ | 2–4 | 8–16 | 0.5–1 |
| NCCLS Expected Result | 2–8 | 1–4 | 1–4 |

TABLE 11

MIC Determinations for *S. aureus*
in SF-P Microplates ™ Containing Resazurin

| | Antimicrobial | | |
|---|---|---|---|
| Diluent | Ampicillin | Kanamycin | Tetracycline |
| Saline | 1–4 | 16–32 | 0.25–2 |
| Gelrite ™ | 1–2 | 16–32 | 0.25–1 |
| NCCLS Expected Results | 0.25–1 | 1–4 | 0.25–1 |

As shown in these tables, the results in the Gelrite™ agreed with the results obtained with saline as an inoculant within one two-fold dilution. This is considered satisfactory according to the National Committee on Clinical Laboratory Standards (NCCLS) guidelines (see e.g., J. Hindler (ed.), "Antimicrobial Susceptibility Testing," in H. D. Isenberg (ed.), *Clinical Microbiology Procedures Handbook*, American Society for Microbiology, pp. 5.0.1 through 5.25.1, [1994]). In one instance, the MIC was slightly lower in saline as compared to Gelrite™. In three instances, the MIC's were slightly lower in Gelrite™, than in saline. Thus, the present invention provides a novel and useful alternative method for determination of antimicrobial sensitivities of microorganisms. Another advantage of this invention is that the test may be conducted in a format that cannot be accidentally spilled.

EXAMPLE 12

Synthesis of Redox Purple

In this Example, the redox indicator referred to as "Redox Purple" was synthesized for use in the present invention. In this Example, the method of Graan et al. (T. Graan, et al., "Methyl Purple, an Exceptionally Sensitive Monitor of Chloroplast Photosystem I Turnover: Physical Properties and Synthesis," Anal Biochem., 144:193–198 [1985]) was used with modifications. This synthesis is shown schematically in FIG. 5 and the Roman numerals (i.e. I,II,III,IV and V) used in this Example refer to those shown in FIG. 5. Unless otherwise indicated, the chemicals used in this Example were obtained from commercial sources such as Sigma.

Figure 5:
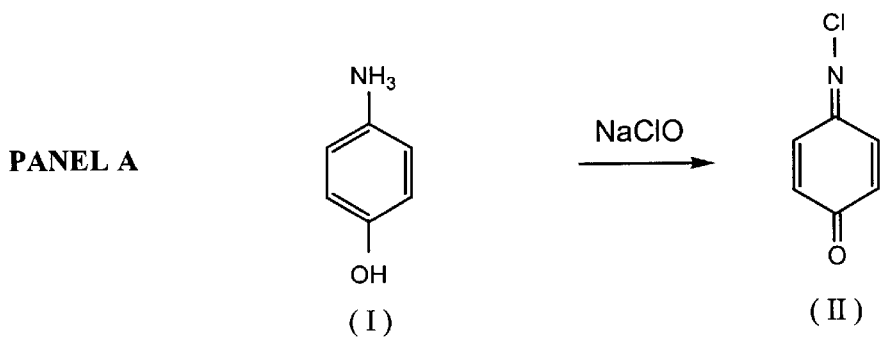
FIG. 5 shows the synthesis pathway of redox purple.
Figure 5:
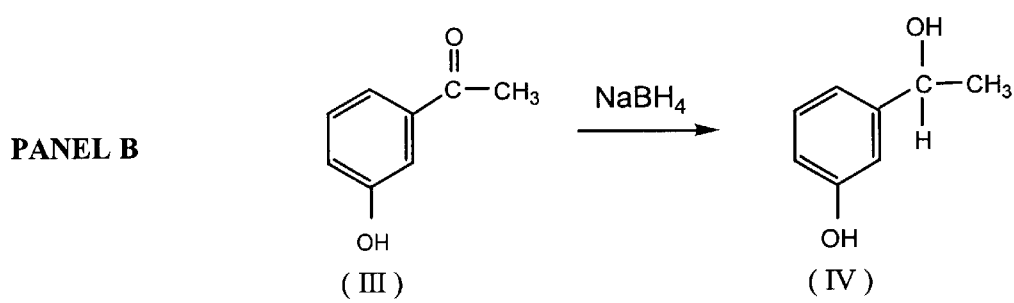
Figure 5:
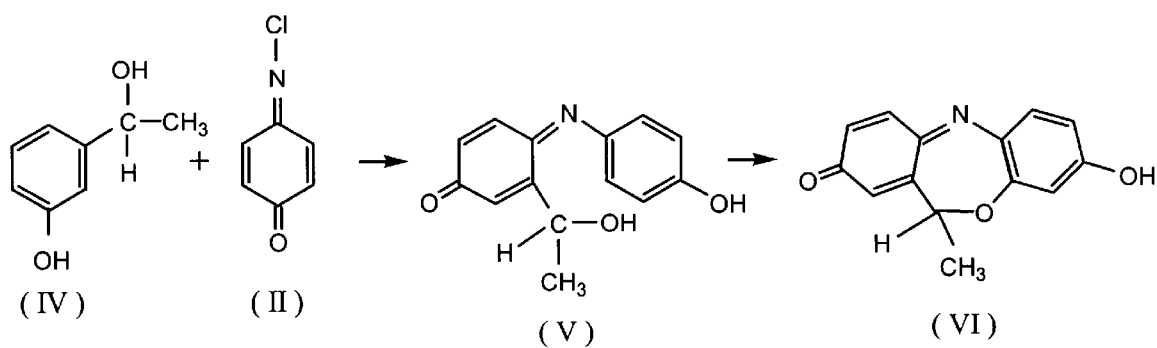

Briefly, the benzoquinone-4-chloroimide (FIG. 5, II) was produced by dissolving 5 g 4-aminophenol (FIG. 5, I) in 1 N aqueous HCl (75 mL) (0° C.), followed by the addition of 200 mL sodium hypochlorite (NaClO, 5% w/v) to produce a chloroimide derivative shown in FIG. 5, Panel A. In this reaction, the solution was continuously stirred and the temperature maintained below 4° C. during addition of the sodium hypochlorite. After stirring at room temperature for 12 hours, the yellow to orange colored product was isolated by filtration, washed with cold distilled water and dried in air and in vacuo. In this step, the product was vacuum filtered using a Buchner funnel, washed with a minimal amount of ice-cold water (approximately 30 ml) in the funnel, dried in air for approximately 24 hours, and dried overnight in a vacuun desiccator.

The synthesis of 1-(3-hydroxyphenyl)-ethanol (FIG. 5, IV) was performed immediately prior to its use, by the reduction of 5 g 1-(3-hydroxyphenyl)-ethanone (available as m-hydroxyacetophenone from Tokyo Kasei Kogyo Co., Ltd. Fukaya, Japan, with TCI America, in Portland, Oreg., being the U.S. distributor) (FIG. 5, III) in water (300 mL) with sodium borohydride ($NaBH_4$, 1.5 g), as shown in FIG. 5, Panel B. The reaction was warmed as necessary to dissolve the starting material and stirred until the evolution of $H_2$ ceased (approximately 1 hour). The pH was decreased to 2.0 (i.e., with concentrated HCl) to remove excess borohydride, followed by addition of 150 ml saturated sodium borate.

The synthesis of redox purple was initiated by addition of the chloroimide derivative (II) to the freshly prepared solution of 1-(3-hydroxyphenyl)-ethanol (IV), in borate buffer ($Na_2B_4O_7/H_3BO_3$). Sodium arsenite ($NaAsO_2$, 10 g) (Sigma) was added to the reaction solution, in order to promote the formation of the indophenol, as well as minimize the occurrence of side reactions. This reaction solution was stirred at room temperature for 2 hours, during which the blue color of the indophenol (FIG. 5, V) appeared. The reaction mixture was then allowed to sit at room temperature for 7–8 days, during which the closure of the heterocyclic ring was allowed to occur due to formation of an oxymethylene group bridge between the two phenolic residues of the quinone-imide. The ring closure was accompanied by a change in the solution color to a dark purple.

The reaction mixture was filtered and the precipitate washed with minimal cold water as described above. The filtrate was saturated with an excess of solid sodium chloride (approximately 100 g), the solution was decanted off the excess salt on the bottom of the container, and the solution extracted with diethylether (5×100 mL) until no more orange-colored material was removed from the aqueous phase. Vigorous shaking of the ether and aqueous phases was avoided, as this was found in some experiments to result in formation of an intractable emulsion. The combined ether layers were back-extracted with 70 mM aqueous sodium carbonate solution (25 mL), the pH of the sodium carbonate solution reduced to 4.5 with glacial acetic acid, and the resulting mixture refrigerated overnight at 4° C. The redox purple precipitated as the free acid. Additional redox purple was obtained by acidifying the original aqueous phases with glacial acetic acid (pH 4.5) and repeating the above purification. The total yield obtained by this synthesis method was approximately 25%.

The purity of the redox purple synthesized according to this method was 95–98%, as determined by thin-layer chromatography, a method that is well know in the art (A. Braithwaite and F. J. Smith, in "Chromatographic Methods" Chapman and Hall [eds.], London [1985], pp. 24–50.). It was found that the redox purple compound was not very soluble in water as the free acid, but was quite soluble in slightly basic solutions (e.g., 1 N $NaHCO_3$), or in organic solvents (e.g. methanol, ethanol, dimethyl sulfoxide [DMSO], dimethyl formamide [DMF], etc.). The compound was observed to be a deep purple color (i.e., of approximately 590 nm as an absorption wavelength) in basic solution and an orange-red color (470 nm) in acidic solution. It is contemplated that analogous derivatives of the reagent (e.g., alkali salts, alkyl O-esters), with modified properties (e.g., solubility, cell permeability, toxicity, and/or modified color(s)/absorption wavelengths) will be produced using slight modifications of the methods described here. It is also contemplated that various forms of redox purple (e.g., salts, etc.), may be effectively used in combination as a redox indicator in the present invention.

EXAMPLE 13

Redox Purple and *E. coli* Identification

In this Example, redox purple was used as the redox indicator in the test system. *E. coli* 287 (ATCC #11775) was cultured overnight at 35° C., on TSA medium supplemented with 5% sheep blood. A sterile, moistened, cotton swab was used to harvest colonies from the agar plate and prepare six identical suspensions of organisms in glass tubes containing 18 ml of 0.85% NaCl, or 0.2% carrageenan type II. The cell density was determined to be 53–59% transmittance. One saline and one carrageenan suspension were used to inoculate Biolog GN Microplates™, with 150 µl aliquots placed into each well. The wells of this plate contain tetrazolium violet as the redox indicator. Two ml of a 2 mM solution of redox purple (sodium salt)(prepared as described in Example 12), or two ml of a 2 mM solution of resazurin (sodium salt) were added to the other tubes, to produce a final dye concentration of 200 µM. These suspensions were used to inoculate Biolog SF-N Microplates™. As with the GN Microplates™, aliquots of 150 µl were added to each well in the plates. The SF-N Microplates™ are identical to the GN MicroPlates™, with the exception being the omission of tetrazolium violet from the wells of the SF-N plates. The inoculated plates were incubated at 35° C. for approximately 16 hours. The plates were then observed and the colors of the well contents recorded.

For the 0.85% NaCl and 0.2% carrageenan suspensions inoculated into the SF-N Microplate™, positive results were obtained for all three redox indicators (i.e., redox purple, tetrazoliun violet, and resazurin) in wells containing the following carbon sources: dextrin, tween-40, tween-80, N-acetyl-D-galactosamine, N-acetyl-D-glucosamine, L-arabinose, D-fructose, L-fucose, D-galactose, α-D-glucose, α-D-lactose, maltose, D-mannitol, D-mannose, D-melibiose, β-methyl-D-glucoside, L-rhamnose, D-sorbitol, D-trehalose, methyl pyruvate, mono-methyl succinate, acetic acid, D-galactonic acid lactone, D-galacturonic acid, D-gluconic acid, D-glucuronic acid, α-ketobutyric acid, D,L-lactic acid, propionic acid, succinic acid, bromosuccinic acid, alaninamide, D-alanine, L-alanine, L-alanyl-glycine, L-asparagine, L-aspartic acid, glycyl-L-aspartic acid, glycyl-L-glutamic acid, D-serine, L-serine, inosine, uridine, thymidine, glycerol, D,L-α-glycerol phosphate, glucose-1-phosphate, and glucose-6-phosphate.

For the 0.85% NaCl and 0.2% carrageenan suspensions, negative results were obtained for all three redox indicators (i.e., redox purple, tetrazolium violet, and resazurin) in wells containing the following carbon sources: α-cyclodextrin, adonitol, D-arabitol, cellobiose, i-erythritol, xylitol, citric acid, D-glucosaminic acid, β-hydroxybutyric acid, γ-hydroxybutyric acid, p-hydroxyphenylacetic acid, itaconic acid, α-ketovaleric acid, malonic acid, quinic acid, sebacic acid, L-histidine, hydroxy L-proline, L-leucine, and D,L-carnitine. The negative control wells containing water, instead of a carbon source were also negative for all three redox indicators.

For glycogen, D-psicose, succinamic acid, and glucuronamide, negative results were obtained with both the 0.85% NaCl and carrageenan suspensions with redox purple. However, positive results were obtained for both suspensions with tetrazolium violet and resazurin.

For gentiobiose, m-inositol, cis-aconitic acid, L-phenylalanine, L-pyroglutamic acid, phenylethylamine, putrescine, 2-amino ethanol, and 2,3-butanediol negative results were obtained with both the 0.85% NaCl and carrageenan suspensions with redox purple and tetrazolium violet. However, positive/negative results were obtained with the 0.2% carrageenan suspension in resazurin, while the resazurin result with the 0.85% NaCl was negative.

For lactulose, D-raffinose, formic acid, α-hydroxybutyric acid, L-glutamic acid, and L-proline, negative results were observed with the 0.85% NaCl suspension tested with redox purple, although the remaining results were positive.

For sucrose and L-ornithine, negative results were obtained for both the 0.85% NaCl and 0.2% carrageenan suspensions tested with redox purple and tetrazolium violet. However, a negative result was observed for the 0.85% NaCl suspension tested with resazurin and a positive result was observed for the 0.2% carrageenan suspension.

For turanose, both the 0.85% NaCl and 0.2% carrageenan suspensions were negative when tested.with redox purple, while the results for both tested with tetrazolium violet were equivocal (+/−), the result for the 0.85% NaCl suspension tested with resazurin was also equivocal (+/−), and the result for the 0.2% carrageenan tested with resazurin was positive.

For α-ketoglutaric acid, negative results were observed for both the 0.85% NaCl and 0.2% carrageenan suspensions tested with redox purple and tetrazolium violet, while positive results were observed for both suspensions tested with resazurin.

For D-saccharic acid, negative results were observed for both the 0.85% and 0.2% carrageenan suspensions tested with redox purple, while the result with tetrazolium violet was equivocal (+/−) for 0.85% NaCl and negative for carrageenan, and the result with resazurin was negative for the 0.85% NaCl and positive for 0.2% carrageenan suspensions.

For L-threonine, equivocal (+/−) results were observed for 0.2% carrageenan suspensions tested with redox purple and tetrazolium violet, while the result with resazurin was positive. For the 0.85% NaCl suspension, the result was negative for redox purple, and positive for tetrazoliun violet and resazurin.

For γ-aminobutyric acid and urocanic acid, negative results were observed for both the 0.85% NaCl and 0.2% carrageenan suspensions tested with redox purple and tetrazolium violet, while equivocal (+/−) results were observed with 0.85% NaCl, and positive results were observed with the 0.2% carrageenan.

In the inoculated GN Microplate™ (containing tetrazolium violet), the wells corresponding to the carbon sources utilized by *E. coli* 287 became either a light or dark purple, while the wells corresponding to the carbon sources not utilized by this organism remained colorless. In contrast, in the inoculated SF-N Microplate™ (containing redox purple), the color pattern was virtually reversed. For negative wells with redox purple, a blue to purple (i.e.,blue-purple, purple-tinged blue, or violet) color was observed. In the SF-N Microplate™ plate, the wells corresponding to carbon sources utilized by this organism were light blue or were colorless, while the wells containing carbon sources not utilized by this organism remained dark blue. The color patterns were easily read and analyzed. Thus, the redox purple was shown to work in a manner that appears to be equivalent to tetrazolium violet for detecting carbon source utilization by bacteria However, there were three colors observed with the plates which included resazurin (ie., blue, pink and colorless), making the redox purple a more useful redox indicator, as there was less ambiguity in the reading of the results.

The observation that none of the wells with redox purple was orange was very surprising, as the literature describing this compound indicated that there was an intermnediate stage in the reduction of the dye which was expected to be reduced through the color progression of blue to orange to colorless. This two-stage reduction is in contrast to the typical reaction observed with resazurin, which gives blue, pink, and colorless wells when analyzed in a like manner. The side-by-side data for the resazurin in this experimnent, as well as other tests, confirms that it does form three colors. The degree to which the results of the various plates were in agreement are shown in the following Table.

TABLE 12

Comparison of Redox Purple and Resazurin with Tetrazolium Violet

| Solution | Dyes Compared | Number of Wells With Same Result (96 Wells/Plate) | % Agreement |
|---|---|---|---|
| Saline | Redox Purple/ Tetrazolium Violet | 85/96 | 88.5 |
| Gel | Redox Purple/ Tetrazolium Violet | 92/96 | 95.8 |
| Saline | Resazurin/ Tetrazolium Violet | 95/96 | 99.0 |
| Gel | Resazurin/ Tetrazolium Violet | 91/96 | 94.8 |

The oxidized form of redox purple spectrally matches the reduced form of tetrazolium violet (i.e., with a maximum absorbance at 590 nm). This may provide an advantage, as detection methods such as spectrophotometry settings may be used interchangeably with tetrazolium violet and redox purple.

EXAMPLE 14

Redox Purple and Identification of Fungi

In this Example, *Aspergillus niger*, *Penicillium chrysogenum*, and *Trichoderma harzianum* were tested using the redox purple redox indicator.

First, the above named organisms were tested using the GN MicroPlate™. However, none of these organisms reduced the tetrazolium violet in the wells of the plate. Thus, redox purple was investigated for use as an alternative dye.

*T. harianum* DAOM 190830 was cultured for seven days at 26° C. on malt extract agar (Difco). A sterile, moistened cotton swab was used to harvest conidia from the culture and prepare a suspension in 16 ml of 0.25% Gelrite™. The cell density was determined to be 75% transmittance. A 2 ml aliquot of a 2 mM solution of redox purple was added to the suspension, along with 2 ml of 1 M triethanolamine-$SO_4$, pH 7.3. The final concentration of redox purple was 200 μM, and the final concentration of triethanolamine-$SO_4$ was 100 mM. The final suspension was mixed well and used to inoculate the wells of a Biolog SF-N Microplate™. In this Example, 100 μl of the suspension was added to each well. The inoculated SF-N Microplate™ was incubated at 30° C. for approximately 24 hours, and observed.

For each carbon source utilized by the organism, the content of the wells was colorless. For each carbon source not utilized by the organism, the content of the wells was blue. In this Example, for this culture, positive results were obtained in the wells containing dextrin, glycogen, tween-40, tween-80, N-acetyl-D-glucosamine, L-arabinose, D-arabitol, cellobiose, i-erythritol, D-fructose, L-fucose, D-galactose, gentiobiose, α-D-glucose, D-mannitol, D-mannose, D-melibiose, β-methyl-D-glucoside, D-sorbitol, D-trehalose, methyl pyruvate, mono-methyl succinate, citric acid, D-galacturonic acid, β-hydroxybutyric acid, α-ketoglutaric acid, quinic acid, sebacic acid, succinic acid, bromo succinic acid, succinamic acid, L-alanine, L-alanyl-glycine, L-asparagine, L-glutamic acid, gylcyl-L-glutamic acid, L-ornithine, L-phenylalanine, L-proline, L-pyroglutamic acid, L-serine, γ-amino butyric acid, inosine, and glycerol.

EXAMPLE 15

Phenotype Analysis of *E. coli*

In this Example, ten strains of *E. coli* were tested and compared in Biolog ES MicroPlates™ and in Biolog Micro-Cards™ containing the same chemistry as the ES Micro-Plates™. The strains tested in this Example are listed in the following Table. As indicated by the designation "H?" in this Table, the H antigen of some of the O157 strains is unknown.

TABLE 13

*E. coli* STRAINS

| Biolog Culture Number | Strain Name |
|---|---|
| 14443 | MG1655 (FB426) |
| 14444 | MG1655 xylA |
| 14445 | MG1655 himA |
| 6320 | W3110 |
| 6321 | MG1655 |
| 6322 | EMG2 (K12, λF⁺) |
| 11547 | O157:H7 |
| 13671 | O157:H? gur+ |
| 13673 | O157:H? |
| 13675 | O157:H? |

All of the strains were cultured overnight on sheep blood agar plates (TSA with 5% sheep blood), at 35° C. Suspensions of the organisms were prepared for testing using either PPS (0.01% Phytagel™, 0.03% pluronic F-58, and 0.45% NaCl) for MicroPlate™ testing, or IF1 (0.2% phytagel, 0.03% pluronic F-68, and 0.25% NaCl) for MicroCard™ testing. All of the strains were tested in both MicroCards™ and MicroPlates™. For MicroPlate™ testing, inocula were prepared in PPS at a density of 63% T (as measured in the Biolog turbidimeter), in 20×150 mm tubes. For Micro-Card™ testing, inocula were prepared in IF1 at a density of 35% T (as measured in the Biolog turbidirneter) in 12×75 tubes. The inocula were dispensed into MicroPlates™ (150 μl/well) or MicroCards™, as appropriate, and incubated at 35° C., for 24 hours. While results were obtained using both the MicroPlates™ and MicroCards™, the results were more consistent with MicroPlates™. Some wells in the Micro-Card™ trapped air bubbles and gave false negative results. The MicroPlate™ results are indicated in Table 14, below, as well as described further in the text following the Table. In Table 14, "+" indicates that the organism tested was capable of utilizing the carbon source listed, while "−" indicates that the organism tested was not capable of utilizing the carbon source listed, and "w" indicates weak positive reactions.

TABLE 14

| Well No. | Carbon Source | \multicolumn{10}{c}{E. coli Strain} | | | | | | | | | |
|---|---|---|---|---|---|---|---|---|---|---|---|
| | | 14443 | 14444 | 14445 | 6320 | 6321 | 6322 | 11547 | 13671 | 13673 | 13675 |
| A1 | Water (control) | − | − | − | − | − | − | − | − | − | − |
| A2 | L-arabinose | + | + | + | + | + | + | + | + | + | + |
| A3 | N-acetyl-D-glucosamine | + | + | + | + | + | + | + | + | + | + |
| A4 | D-saccharic acid | + | + | + | + | + | + | − | − | − | − |
| A5 | Succinic acid | + | + | + | + | + | + | + | + | + | + |
| A6 | D-galactose | + | + | + | + | + | + | + | + | + | + |
| A7 | L-aspartic acid | + | + | + | − | + | + | + | + | + | + |
| A8 | L-proline | w | − | w | + | + | + | + | + | + | + |
| A9 | D-alanine | + | + | + | + | + | + | + | + | + | + |
| A10 | D-trehalose | + | + | + | + | + | + | + | + | + | + |
| A11 | D-mannose | + | + | + | + | + | + | + | + | + | + |
| A12 | Dulcitol | − | − | − | − | + | − | + | + | − | + |
| B1 | D-serine | + | + | + | + | + | + | w | − | w | w |
| B2 | D-sorbitol | + | + | + | + | + | + | − | − | − | − |
| B3 | Glycerol | − | − | − | + | + | + | + | + | + | + |
| B4 | L-fucose | + | + | + | + | + | + | + | + | + | + |
| B5 | D-glucuronic acid | + | + | + | + | + | + | + | + | + | + |
| B6 | D-gluconic acid | + | + | + | + | + | + | + | + | + | + |
| B7 | D,L-α-glycerol phosphate | − | − | − | − | + | + | + | + | + | + |
| B8 | D-xylose | + | − | + | + | + | + | + | + | + | + |
| B9 | L-lactic acid | + | + | + | + | + | + | + | + | + | + |
| B10 | Formic acid | + | + | + | + | + | + | + | + | − | + |
| B11 | D-mannitol | + | + | + | + | + | + | + | + | + | + |
| B12 | L-glutamic acid | + | − | − | − | − | w | − | + | + | + |
| C1 | Glucose-6-phosphate | + | + | + | + | + | + | + | + | + | + |
| C2 | D-galactonic acid-γ-lactone | + | + | + | − | + | + | − | − | − | − |
| C3 | D,L-malic acid | + | + | + | + | + | + | + | + | + | + |
| C4 | D-ribose | + | + | + | + | + | + | + | + | + | + |
| C5 | Tween-20 | − | − | − | − | w | w | w | w | w | w |
| C6 | L-rhamnose | + | + | + | + | + | + | + | + | + | w |
| C7 | D-fructose | + | + | + | + | + | + | + | + | + | + |
| C8 | Acetic acid | + | + | + | + | + | + | + | + | + | + |
| C9 | α-D-glucose | + | + | + | w | + | + | + | + | + | + |
| C10 | Maltose | + | − | − | + | + | + | + | + | + | + |
| C11 | D-melibiose | + | + | + | + | + | + | + | + | + | + |
| C12 | Thymidine | + | + | + | + | + | + | + | + | + | + |
| D1 | L-asparagine | + | + | + | − | + | + | + | + | + | + |
| D2 | D-aspartic acid | − | − | − | − | − | − | − | − | − | − |
| D3 | D-glucosaminic acid | − | − | − | − | − | − | − | − | − | − |
| D4 | 1,2-propanediol | − | − | − | − | − | − | − | − | − | − |
| D5 | Tween-40 | − | − | − | w | w | w | w | w | w | w |
| D6 | α-ketoglutaric acid | + | + | + | + | + | + | − | + | + | + |
| D7 | α-ketobutyric acid | + | + | − | + | + | − | w | − | − | − |
| D8 | α-methyl galactoside | + | + | + | + | + | + | + | + | + | + |
| D9 | α-D-lactose | + | + | + | + | + | + | + | + | + | + |
| D10 | Lactulose | − | − | − | − | − | + | + | + | + | + |
| D11 | Sucrose | − | − | − | − | − | − | − | + | + | + |
| D12 | Uridine | + | + | + | + | + | + | + | + | + | + |
| E1 | L-glutamine | + | + | + | − | − | + | + | + | + | + |
| E2 | M-tartaric acid | − | − | − | − | − | − | w | + | − | − |
| E3 | Glucose-1-phosphate | + | + | + | + | + | + | + | + | + | + |
| E4 | Fructose-6-phosphate | + | + | + | + | + | + | + | + | + | + |
| E5 | Tween-80 | − | − | − | w | + | w | w | w | w | w |
| E6 | α-hydroxyglutaric acid γ-lactone | − | − | − | − | w | − | w | − | − | w |
| E7 | α-hydroxy butyric acid | + | + | − | + | + | + | w | w | w | w |
| E8 | β-methyl glucoside | + | + | + | + | + | + | + | + | + | + |
| E9 | Adonitol | − | − | − | − | − | − | − | − | − | − |

TABLE 14-continued

| Well No. | Carbon Source | \multicolumn{10}{c}{*E. coli* Strain} |
|---|---|---|---|---|---|---|---|---|---|---|---|
| | | 14443 | 14444 | 14445 | 6320 | 6321 | 6322 | 11547 | 13671 | 13673 | 13675 |
| E10 | Maltotriose | + | − | − | + | + | + | + | + | + | + |
| E11 | 2'-deoxy-adenosine | + | + | + | + | + | + | + | + | + | + |
| E12 | Adenosine | + | + | + | + | + | + | + | + | + | + |
| F1 | Glycyl-L-aspartic acid | + | + | + | + | + | + | + | + | + | + |
| F2 | Citric acid | − | − | − | − | − | − | − | − | − | − |
| F3 | M-inositol | − | − | − | − | − | − | − | − | − | − |
| F4 | D-threonine | − | − | − | − | − | − | − | − | − | − |
| F5 | Fumaric acid | + | + | + | + | + | + | + | + | + | + |
| F6 | Bromo succinic acid | + | + | + | + | + | + | + | + | + | + |
| F7 | Propionic acid | + | + | − | + | + | + | + | + | + | + |
| F8 | Mucic acid | + | + | + | + | + | + | + | + | + | + |
| F9 | Glycolic acid | + | + | − | + | + | + | − | − | − | − |
| F10 | Glyoxylic acid | w | w | w | + | + | + | + | − | − | − |
| F11 | Cellobiose | − | − | − | − | − | − | − | − | − | − |
| F12 | Inosine | + | + | + | + | + | + | + | + | + | + |
| G1 | Glycyl-L-glutamic acid | + | + | + | + | + | + | + | + | + | + |
| G2 | Tricarballylic acid | − | − | − | − | − | − | − | − | − | − |
| G3 | L-serine | + | + | + | + | + | + | + | + | + | + |
| G4 | L-threonine | + | − | − | − | − | + | − | w | w | w |
| G5 | L-alanine | + | + | + | + | + | + | + | + | + | + |
| G6 | L-alanyl-glycine | + | + | + | + | + | + | + | + | + | + |
| G7 | Acetoactetic acid | − | − | − | w | − | − | − | − | − | − |
| G8 | N-acetyl-β-D-mannosamine | − | − | w | w | − | + | + | w | w | + |
| G9 | Mono-methyl succinate | + | + | + | + | + | + | + | + | + | + |
| G10 | Methyl pyruvate | + | + | + | + | + | + | + | + | + | + |
| G11 | D-malic acid | + | + | + | + | + | + | + | + | + | w |
| G12 | L-malic acid | + | + | + | + | + | + | + | + | + | + |
| H1 | Glycyl-L-proline | + | + | + | + | + | + | + | + | + | + |
| H2 | P-hydroxy phenylacetic acid | − | − | − | − | − | − | − | − | − | − |
| H3 | M-hydroxyphenyl acetic acid | − | − | − | − | − | − | − | − | − | − |
| H4 | Tyramine | − | − | − | − | − | − | − | − | − | − |
| H5 | D-psicose | + | + | + | + | + | + | + | + | + | + |
| H6 | L-lyxose | − | − | − | − | + | + | − | − | − | − |
| H7 | Glucuronamide | + | + | + | + | + | + | + | + | + | + |
| H8 | Pyruvic acid | + | + | + | + | + | + | + | + | + | + |
| H9 | L-galactonic acid γ-lactone | + | + | + | + | + | + | + | + | + | + |
| H10 | D-galacturonic acid | + | + | + | + | + | + | + | + | + | + |
| H11 | Phenylethyl amine | − | − | − | − | − | − | − | − | − | − |
| H12 | 2-amino ethanol | − | − | − | − | − | − | − | − | − | − |

Strains 14443 and 14444

Strain 14444 has been reported to be a xylA (i.e., xylose-negative) mutant of strain 14443. The results of this experiment indicated that while strain 14443 is xylose-positive (i.e., capable of utilizing xylose), strain 14444 is xylose-negative (i.e., incapable of utilizing xylose) However, strain 1444 was found to be negative also for maltose, maltotriose, L-proline, and L-threonine. While the results observed with L-proline and L-threonine may not be significant as these traits have been observed to be inconsistent between strains, the results obtained with maltose and maltotriose are significant, as discussed below.

Strains 14443 and 14445

Strain 14445 has been reported to be an himA mutant of strain 14443. Prior to this experiment, it was unknown what phenotypic changes due to the himA allele, would be observed in 14445, as compared with strain 14443. Differences between 14443 and 14445 were observed in eight tests. Strain 14445 was negative for utilization of maltose, maltotriose, α-ketobutyric acid, x-hydroxybutyric acid, propionic acid, glycolic acid, L-glutainc acid, and L-threonine. Although the results observed for L-glutamic acid and L-threonine may not be significant, as these traits have been observed to be inconsistent between strains, the results observed with maltose and maltotriose indicate the presence of a defect in maltose metabolism, as also observed in strain 14444. This was confirmed by contacting the source of these strains, Dr. Jeremy Glasner (in Dr. Fred Blattner's laboratory, at the University of Wisconsin), who tested these strains and confirmed that these strains had accidentally acquired a maltose metabolism defect when he prepared a batch of competent cells. Without the results of the present experiment, the accidentally introduced defect would have gone unrecognized. With regard to the defects in utilization of the other four carbon sources, it appears that the himA allele may make cells deficient in utilization of α-hydroxy acids, a new and surprising observation, that has been heretofore unrecognized.

Strains 14443 and 6321

These strains are supposed to be the same strain, and both were obtained from Dr. Barbara Bachmann, at the *E. coli* Genetic Stock Center. Prior to testing in this experiment, strain 14443 was maintained by Dr. Blattner's laboratory, while strain 6321 was stored at Biolog. As indicated in Table 14, these two strains were shown to have differences, some of which may be insignificant, but some of which may have resulted from improper storage and maintenance, which caused the culture to change over time.

Strains 6322, 6321, and 6320

Strain 6322 is the originating strain of the genetically important *E. coli* K12 culture. Strains 6321 and 6320 were reported as being derived from 6322 via genetic manipulations that eliminated the lambda phage and F+episome. Strain 6321 was created using careful genetic manipulations, and as indicated in Table 14, its pattern of carbon utilization observed in this experiment was very similar to that of strain 6322. However, strain 6320 was created through harsh treatment (exposure to X-rays), and it differs from strain 6322 in many traits.

Strains 11547, 13671, 1367, and 13675

These strains are all of the O157 serological line, and are considered to be human pathogens. These strains are similar to each other, but are rather different from the K-12 strains. It is well known that most O157 strains are sorbitol negative, and this was observed for these four strains. However, it was also found that these strains have other special traits. For example, all four of these strains were also negative for D-saccharic acid, and D-galactonic acid-g-lactone. In addition, three of the four strains were positive. for sucrose. The negative result observed for D-galactonic acid-g-lactone is particularly interesting. The genes involved in metabolism of D-galactonic acid-g-lactone (dgo) map at 82 minutes on the *E. coli* genome. Recent genome sequencing data have indicated that in at least one O157 strain, a large "pathogenicity island" has been inserted in the *E. coli* genome at 82 minutes. It is possible that the insertion of this pathogenicity island may have resulted in the inactivation of the dgo genes.

EXAMPLE 16

Phenotypic Analysis of Yeast

In this Example, yeast are analyzed for phenotypic differences using the Biolog YT MicroPlate™. *S. cerevisiae* strains are grown on suitable media (e.g., as described in Example 9), and inoculated into the wells of the YT MicroPlate™ as described in Example 9. The ability of the strains to utilize different carbon sources (e.g., D-galactose) is then observed and compared, in order to assess the phenotypic differences between the strains. As indicated in Example 9, water or Gelrite™ may be used as the inoculation suspension medium, as well as 0.85% NaCl or PPS (e.g., as described in Example 15), above with 100 μl inoculated per well, rather than the 150 μl used with bacteria.

EXAMPLE 17

Kinetic Analysis

In this Example, two *E. coli* strains constructed so as to be isogenic with the exception of a single allele are compared for their ability to utilize 95 different carbon sources in the Biolog ES MicroPlate™. The strains are cultured under identical conditions by growing them at room temperature on blood agar plates (TSA with 5% sheep blood). Suspensions are prepared in PPS, as described in Example 15, above. Then, 150 μl of the suspensions are used to inoculate all of the wells of two ES MicroPlates™ (i.e., one MicroPlate™ for each strain). The metabolic response (i.e., purple color formation) is followed kinetically at room temperature in a microplate reader (erg., the Biolog MicroStation™) for a 24-hour period, and recorded, using SOFTmax® OPRO software (Molecular Devices). Kinetic measurements are made using one of two methods. In the first method, each of the two MicroPlates™ are placed inside a kinetic microplate reader and read at 15 minute intervals over a 24hour period. In the second method, each of the two MicroPlates™ are cycled in and out of a microplate reader using a ROBOmax® in-feed stacking device (Molecular Devices). The MicroPlates™ are read at 15 minute intervals over a 24-hour period. The kinetic readings are then converted into 24-hour kinetic response patterns. The two patterns obtained are compared, in order to identify differences in the organisms' responses to each of the 95 carbon sources tested.

EXAMPLE 18

Testing for Growth Stimulation by Nitrogen, Phosphorus, and Sulfur Sources, and Other Nutrients In this Example, experiments to assess the ability of *E. coli* to utilize various nitrogen, sulfur, and phosphorus sources were conducted using the methods described above. For these experiments, *E. coli* MG1655, kindly provided by Dr. Fred Blattner (University of Wisconsin, Madison), was used. In addition to the *E. coli* strain, two *Salmonella typhimurium* auxotrophs (histidine and pyrimidine; available from Salmonella Genetic Stock Center, University of Calgary, Calgary, Alberta) were tested.

Prior to inoculating MicroPlate™ microtiter plates, MG1655 was pre-grown overnight on the limited nutrient medium, R2A (Acumedia). MG1655 cells were streaked onto the R2A agar, and grown overnight at 35° C. Individual colonies were picked from the agar surface, using a sterile cotton swab. The cells were suspended in GN/GP-IF inoculating fluid (Biolog), at a density corresponding to 50% transmittance in a turbidimeter (Biolog), using a 20 mM diameter tube. The suspension was then diluted 8-fold, and inoculated onto the MicroPlate™ microtiter plates. Three panels of MicroPlates™ were used in these experiments, designated "EN" (used for testing nitrogen sources), "EPS" (used for testing phosphorous and sulfur sources), and "EA" (used in the auxotrophic testing experiments). The plates were incubated at 35° C. under humid conditions for 48 hours, at which time sufficient purple color had developed in the positive control wells, while the negative control wells remained colorless. During these experiments that suspensions diluted between 4–16-fold gave the most accurate readings. More turbid solutions resulted in false positive reactions, while less turbid solutions took too long to develop color.

It was determined during the course of these experiments that pre-growth of the cells on R2A was sufficient to deplete the nutrient reserves of the organisms, such that subsequent growth in the MicroPlate™ microtiter plates was entirely dependent upon the nutritional supplements provided in each of the wells. Indeed, R2A was chosen after careful examination of a number of pre-growth media, including Luria-Bertani (LB), TSA, TSA with 5% sheep blood, BUG™ (Biolog), and BUG™ with blood. Organisms pre-cultured on R2A were the only cultures that exhibited no growth and therefore, no purple color in the negative control wells (ie., wells that did not contain either a nitrogen source ["N-free" well], a phosphorus source ["P-free" well], or a sulfur source ["S-free" well]).

The complete minimal medium used in the MicroPlate™ microtiter plates contained 100 mM NaCl, 30 mM triethanolamine-HCl (pH 7.1), 25 mM sodium pyruvate, 5.0 mM $NH_4Cl$, 2.0 mM $NaH_2PO_4$, 0.25 mM $Na_2SO_4$, 0.05 MM $MgCl_2$, 1.0 mM KCl, 1.0 μM ferric chloride, and 0.01% tetrazolium violet. The ability of MG1655 to grow on the defined medium served as a positive control in each experiment. For auxotrophic testing in the EA panel, this medium was supplemented with various nutrients and/or growth factors, with vitamins and Tweens provided at 0.25 μM, nucleotides/nucleosides at 100 μM, amino acids at 10 μM, N-α-acetyl-L-ornithine, L-ornithine, L-citrulline, putrescine, spermidine, and spermine at 50 μM; and 4-amino-imidazole-4(5)-carboxamide at 1 mM. For testing various nitrogen sources (i.e., in the EN panel), the $NH_4Cl$ in the medium was replaced with 3.0 mM of the nitrogen source being examined. For phosphorus and sulfur source testing on the EPS panel, the $NaH_2PO_4$ or $Na_2SO_4$ in the medium were replaced with 1.0 mM or 100 μM respectively, of the various phosphorus and sulfur sources tested. In all cases, the pH of the stock solutions containing the various test chemicals was tested, and if necessary, adjusted to approximately pH 7 with either NaOH or HCl, prior to dispensing the chemicals in the appropriate test panel(s). All of the chernicals tested were obtained from Sigma.

Nitrogen-free, sulfur-free, and phosphorous-free media were used in the negative control wells of the EN and EPS panels, and consisted of the defined minimal medium described above, with the omission of $NH_4Cl$, $NaH_2PO_4$, or $Na_2SO_4$. Lack of growth/purple color in the negative control wells indicated the absence of significant quantities of nitrogen, phosphorous and sulfur-containing contaminants that might have been present due to transfer of these elements when the organisms were inoculated in the wells of the MicroPlate™ microtiter plates from the R2A medium.

The nitrogen sources tested included ammonium chloride, sodium nitrite, potassium nitrate, urea, glutathione (reduced form), alloxan, L-citrulline, putrescine, L-ornithine, agmatine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-tyrosine, L-threonine, L-valine, D-alanine, D-asparagine, D-aspartic acid, D-glutamic acid, D-lysine, D-serine, D-valine, N-acetyl-glycine, L-pyroglutamic acid, L-homoserine, met-ala, n-amylamine, n-butylamine, ethylamine, ethanolamine, ethylene diamine, histamine, (R)-(+)-α-phenylethylamine, β-phenylethylamine, tyramine, acetamide, formamide, glucuronamide, lactamide, D(+)-glucosamine, D(+)-galactosamine, D-mannosamine, N-acetyl-D-glucosamine, N-acetyl-D-galactosamine, N-acetyl-D-mannosamine, adenine, adenosine, cytosine, thymine, thymidine, uracil, uridine, xanthine, xanthosine, inosine, DL-α-amino-n-butyic acid, γ-amino-n-butyric acid, ε-amino-n-caproic acid, DL-α-amino-caprylic acid, hippuric acid, parabanic acid, uric acid, urocanic acid, δ-amino-n-valeric acid, 2-amino-valeric acid, gly-glu, ala-gly, ala-his, ala-thr, gly-met, gly-gln, ala-gIn, gly-ala, and gly-asn.

The phosphorus sources tested included phosphate, pyrophosphate, trimetaphosphate, tripolyphosphate, hypophosphite, thiophosphate, adenosine 2'-monophosphate, adenosine 3'-monophosphate, adenosine 5'-monophosphate, adenosine 2':3'-cyclic monophosphate, adenosine 3':5'-cyclic monophosphate, dithiophosphate, DL-α-glycero-phosphate, β-glycero-phosphate, phosphatidyl glycerol, phosphoenol pyruvate, phosphocreatine, 2' deoxy glucose 6-phosphate, guanosine 2'-monophosphate, guanosine 3'-monophosphate, guanosine 5'-monophosphate, guanosine 2':3'-cyclic monophosphate, guanosine 3':5'-cyclic monophosphate, glucose 1-phosphate, glucose 6-phosphate, fructose 1-phosphate, fructose 6-phosphate, mannose 1-phosphate, mannose 6-phosphate, arabanose 5-phosphate, cytidine 2'-monophosphate, cytidine 3'-monophosphate, cytidine 5'-monophosphate, cytidine 2':3'-cyclic monophosphate, cytidine 3':5'-cyclic monophosphate, glucosamine 1-phosphate, glucosamine 6-phosphate, phospho-L-arginine, O-phospho-D-serine, O-phospho-L-serine, O-phospho-D-tyrosine, O-phospho-L-tyrosine, uridine 2'-monophosphate, uridine 3'-monophosphate, uridine 5'-monophosphate, uridine 2':3'-cyclic monophosphate, uridine 3':5'-cyclic monophosphate, O-phospho-L-threonine, inositol hexaphosphate, nitrophenyl phosphate, 2-aminoethyl phosphonate, 6-phosphogluconic acid, 2-phosphoglyceric acid, phospho-glycolic acid, phosphonoacetic acid, thymidine 3'-monophosphate, thymidine 5'-monophosphate, methylene diphosphonic acid, and thymidine 3':5'-cyclic monophosphate.

The sulfur sources tested included sulfate, thiosulfate, tetrathionate, thiophosphate, dithiophosphate, L-cysteine, cys-gly, L-cysteic acid, cysteamine, L-cysteine-sulphinic acid, cystathionine, lanthionine, DL-ethionine, glutathione (reduced form), L-methionine, glycyl-DL-methionine, S-methyl-L-cysteine, L-methionine sulfoxide, Lmethionine sulfone, taurine, N-acetyl-DL-methionine, N-acetyl cysteine, isethionate, thiourea, thiodiglycol, thioglycolic acid, thiodiglycolic acid, 1-dodecane-sulfonic acid, taurocholic acid, tetramethylene sulfone, hypotaurine, O-acetyl-serine, 3':3' thiodipropionic acid, L-djenkolic acid, and 2-mercaptoethylamine.

The auxotrophic supplements tested included L-alanine, L-arginine, L-asparagine, L-aspartic acid, adenine, adenosine, 2'-deoxyadenosine, adenosine 3':5'-cyclic monophosphate, adenosine 3'-monophosphate, adenosine 5'-monophosphate, L-cysteine, L-glutamic acid, L-glutamine, L-glycine, L-histidine, L-isoleucine, guanine, guanosine, 2'-deoxyguanosine, guanosine 3':5'-cyclic monophosphate, guanosine 3'-monophosphate, guanosine 5'-monophosphate, L-leucine, L-lysine, L-methionine, L-phenylalanine, L-proline, L-serine, cytosine, cytidine, 2'-deoxycytidine, cytidine 3':5'-cyclic monophosphate, cytidine 3'-monophosphate, cytidine 5'-monophosphate, Itryptophan, Ltyrosine, L-threonine, L-valine, D-alanine, D-aspartic acid, thymine, thymidine, thymidine 3':5'-cyclic monophosphate, thymidine 3'-monophosphate, thymidine 5'-monophosphate, D-glutamic acid, (5)4-amino-imidazole-4(5)-carboxamide, DL-α,ε-diaminopimelic acid, D-biotin, DL-α-lipoic acid, caprylic acid, uracil, uridine, 2'-deoxyuridine, uridine 3':5'-cyclic monophosphate, uridine 3'-monophosphate, uridine 5'-monophosphate, p-aminobenzoic acid, shikimic acid, molybdic acid, folic acid, α-keto-isovaleric acid, D-pantothenic acid, hypoxanthine, inosine, 2'-deoxyinosine, inosine 3':5'-cyclic monophosphate, inosine 3'-monophosphate, inosine 5'-monophosphate, thiamine, riboflavin, pyridoxal, pyridoxine, pyridoxamine, quinolinic acid, glutathione (reduced form), L-homoserine lactone, α-ketobutyric acid, β-nicotinamide adenine dinucleotide, nicotinic acid, nicotinamide, N-α-acetyl-L-ornithine, L-ornithine, L-citrulline, putrescine, spermidine, spermine, Tween 20, Tween 40, Tween 60, Tween 80, and δ-amino-levulinic acid.

Following approximately 48 hours of incubation, the inoculated test panels were observed. For the nitrogen, phosphorus and sulfur tests, the contents of the wells in which *E. coli* was able to grow (i.e., the well contained a nitrogen, phosphorus, or sulfur source suitable for the organism) turned purple. In the auxotrophic test panel (EA), phenotypes that were stimulated by histidine or various pyrimidine compounds produced a purple color in the wells where Salmonella was growth was stimulated.

For MG1655 tested in the EN panel, the following compounds served as suitable nitrogen sources, as indicated by a "positive" result: positive control (medium with NH$_4$Cl), L-arginine, L-asparagine, L-aspartic acid, L-glutamic acid, L-glutamine, glycine, L-proline, D-alanine, L-proline, D-alanine, D(+)-glucosamnine, N-acetyl-D-glucosamine, δ-amino-n-valeric acid, gly-glu, ala-gly, ala-thr, gly-met, gly-gln, ala-gln, gly-ala, and gly-asn. The following compounds resulted in a weak positive test result: D(+)-galactosamine, D-mannosamine, and γ-amino-n-butyric acid. The following compounds were not suitable nitrogen sources (i.e., there was no MG1655 growth in wells containing these compounds: negative control (medium without any nitrogen source), sodium nitrite, potassium nitrate, urea, glutathione (reduced form), alloxan, L-citrulline, putrescine, L-ornithine, agmatine, L-alanine, L-cysteine, L-histidine, L-isoleucine, L-leucine, L-lysine, L-methionine, L-phenylalanine, L-serine, L-tyrosine, L-threonine, L-valine, D-asparagine, D-aspartic acid, D-glutamic acid, D-lysine, D-serine, D-valine, N-acetyl-glycine, L-pyroglutamic acid, L-homoserine, met-ala, n-amylamine, n-butylamine, ethylamine, ethanolamine, ethylenediamine, histamine, (R)-(+)-α-phenylethylamine, P-phenylethylamine, tyramine, acetamide, formamide, glucuronamide, lactamide, N-acetyl-D-galactosamine, N-acetyl-D-mannosamine, adenine, adenosine, cytosine, thymine, thymidine, uracil, uridine, xanthine, xanthosine, inosine, DL-α-amino-n-butyric acid, γ-amino-n-butyric acid, ε-amino-n-caproic acid, DL-α-amino-caprylic acid, hippuric acid, parabanic acid, uric acid, urocanic acid, 2-amino-valeric acid, and ala-his.

For the phosphorus and sulfur test panel (EPS), the following compounds served as suitable phosphorus or sulfur sources, as indicated by a "positive" result: positive phosphate control (medium with phosphate), positive sulfur control (medium with sulfate), trimetaphosphate, thiophosphate, hypophosphite, adenosine-2'-monophosphate, adenosine 3-monophosphate, dithiophosphate, DL-α-glycerophosphate, β-glycerophosphate, phosphoenol pyruvate, phosphocreatine, 2'-deoxyglucose 6-phosphate, guanosine 2'-monophosphate, guanosine 3'-monophosphate, guanosine 5'-monophosphate, guanosine 2':3'-cyclic monophosphate, glucose 1-phosphate, glucose 6-phosphate, fructose 1-phosphate, fructose 6-phosphate, mannose 1-phosphate, mannose 6-phosphate, arabinose 5-phosphate, cytidine 3'-monophosphate, cytidine 5'-monophosphate, cytidine 2':3'-cyclic monophosphate, glucosamine 1-phosphate, glucosamine 6-phosphate, phospho-L-arginine, O-phospho-D-serine, O-phospho-L-serine, O-phospho-D-tyrosine, O-phospho-L-tyrosine, uridine 2'-monophosphate, uridine 3'-monophosphate, uridine 5'-monophosphate, uridine 2':3'-cyclic monophosphate, O-phospho-L-threonine, 6-phosphogluconic acid, 2-phosphoglyceric acid, phosphoglycolic acid, thymnidine 3'-monophosphate, thymidine 5'-monophosphate, thiosulfate, tetrathionate, thiophosphate, dithiophosphate, L-cysteine, cys-gly, L-cysteic acid, L-cysteine sulphinic acid, cystathionine, lanthionine, glutathione, L-methionine, glycyl-DL-methionine, Lmethionine sulfoxide, taurine, N-acetyl-DL-methionine, isethionate, taurocholic acid, hypotaurine, O-acetyle-serine with sodium sulfate, L-djenkolic acid. The following compounds resulted in a weak positive test result: 2-aminoethyl phosphonate, S-methyl-L-cysteine. The following compounds were not suitable phosphorous or sulfur sources (i.e., there was no MG1655 growth in wells containing these compounds: negative control (medium without any phosphorus or sulfur source), pyrophosphate, tripolyphosphate, adenosine 5'-monophosphate, adenosine 2':3'-cyclic monophosphate, adenosine 3':5'-cyclic monophosphate, phosphatidyl glycerol, guanosine 3':5'-cyclic monophosphate, cytidine 2'-monophosphate, cytidine 3':5'-cyclic monophosphate, uridine 3':5'-cyclic monophosphate, inositol hexaphosphate, nitrophenyl phosphate, phosphonoacetic acid, methylene diphosphonic acid, thymidine 3':5'-cyclic monophosphate, DL-ethionine, L-methionine sulfone, N-acetyl cysteine, thiourea, thiodiglycol, thioglycolic acid, thiodiglycolic acid, 1-dodecane-sulfonic acid, and tetramethylene sulfone.

Finally, as MG1655 is not auxotrophic for any nutrients or growth factors, this strain was capable of growing in all wells of the EA panel. Instead, two *S. typhimurium* auxotrophs were used in the EA experiments. With one strain, hisF645, only the well containing L-histidine turned purple, while with the other strain, pyrCΔ73, wells containing a pyrimidine (i.e., uracil, cytosine, uridine, cytidine, 2-deoxyuridine, 2-deoxycytidine, uridine 3'-monophosphate, uridine 5'-monophosphate, cytidine 2'-monophosphate, cytidine 3'-monophosphate, and cytidine 5'-monophosphate) turned purple and wells containing a purine (i.e., adenosine 2'-monophosphate, adenosine 3'-monophosphate, adenosine S'-monophosphate, guanosine 2'-monophosphate, guanosine 5'-monophosphate, guanine, inosine, 2'-deoxyadenosine, and 2' deoxyguanosine), turned weakly purple. These results demonstrated the appropriate stimulation of organism growth.

From the above Examples, it is clear that the present invention represents an unexpected and much improved system for the broad-based, rapid biochemical testing and/or phenotypic testing of microorganisms and/or other cell types, in many uses and formats (or configurations). In one embodiment, the present invention provides a major advance in the testing of actinomycetales, fungi, and other spore-forming microorganisms. The results are highly surprising in view of the obligate aerobic nature of most of these organisms. Using the novel approach of embedding the organisms in a gel matrix, the biochemical test reactions are dispersed uniformly throughout the testing well, providing an easy to read indicator of organism growth and metabolism. In addition, both automated and manual systems with fixed time point or kinetic reading may be used in conjunction with the present invention. For example, the results may be observed visually (i.e., by eye) by the person conducting the test, without assistance from a machine. Alternatively, the results may be obtained with the use of equipment (e.g., a microtiter plate reader) that measures transmittance, absorbance, or reflectance through, in, or from each well of a multitest device such as a microtiter testing plate (e.g., MicroPlate™) or a miniaturized testing card (e.g., MicroCard™). Kinetic readings may be obtained by taking readings at frequent time intervals or reading the test results continuously over time. One example of a device particularly suited for incubating and conducting the methods of the present invention includes the device described in co-pending U.S. patent application Ser. No. 09/277,353.

In other embodiments, the present invention provides methods and compositions for easily performing comparative testing of numerous phenotypes, thereby providing means to determine the functions of various genes.

In summary, the embodiments of the present multitest gel-matrix invention provide numerous advances and advantages over the prior art, including: (1) much greater safety, as there is no spillage, nor aerosolization of cells, mycelia, nor spores, while performing or inoculating test wells; (2) faster biochemical reactions are produced, giving final results hours or days earlier than commonly used methods; (3) more positive biochemical reactions are obtained, giving a truer picture of the microorganisms' metabolic characteristics; (4) darker, more clear-cut biochemical reactions and color changes are obtained; (5) more uniform color and/or turbidity are obtained, as the cells, mycelia, and/or spores do not settle and clump together at the bottom of the wells, nor do they adhere to the sides of the wells; (6) the reactions are much easier to observe visually or with optical instruments (e.g., the Biolog MicroStation Reader™); and (7) the overall process for performing multiple tests is extremely simple and efficient, requiring very little labor on the part of the microbiologist. All of these advantages enhance the speed and accuracy of scoring test results in studies to characterize and/or identify microorganisms, or to perform comparative phenotypic analysis of any cell type, including microbial strains.

What is claimed is:

1. A testing system for measuring at least 95 nutritional phenotypes of at least one cell type, comprising a testing device having a plurality of testing wells wherein said testing wells contain at least one test substrate selected from the group consisting of nitrogen sources selected from the group consisting of nitrogen-containing compounds, phosphorus sources selected from the group consisting of phosphorus-containing compounds, sulfur sources selected from the group consisting of sulfur-containing compounds, and auxotrophic supplements selected from the group consisting of amino acids, vitamins, polyamines, lactones, fatty acids, nucleic acid bases, nucleosides and nucleotides; inoculating fluid comprising a gelling agent, under conditions such that said gelling agent remains ungelled; and an instrument capable of incubating and recording the response of said at least one cell type placed in said testing device.

2. The testing system of claim 1, wherein said nitrogen sources are selected from the group consisting of D-alanine, L-alanine, L-arginine, D-asparagine, L-asparagine, D-aspartic acid, L-aspartic acid, L-cysteine, L-cystine, D-glutamic acid, L-glutamic acid, L-glutamine, glycine, L-histidine, L-homoserine, D,L-β-hydroxy-glutamic acid, L-isoleucine, L-leucine, L-phenylalanine, L-proline, D-serine, L-serine, L-tryptophan, L-tyrosine, glutathione, cytosine, D-glucosamine, D-galactosamine, D-mannosamine, N-acetyl-D-glucosamine, N-acetyl-D-galactosamine, N-acetyl-D-mannosamine, methylamine, ethylamine, butylamine, isobutylamine, amylamine, ethanolamine, ethylenediamine, pentamethylenediamine, hexamethylenetriamine, phenylethylamine, tyramine, piperidine, pyrrole, β-alanine, acetylglycocol, phenylglycine-o-carbonic acid, α-aminovaleric acid, γ-aminovaleric acid, α-aminoisovaleric acid, γ-aminoisovaleric acid, α-aminocaproic acid, γ-aminocaprylic acid, acetamide, lactamide, glucuronamide, formamide, propionamide, methoxylamide, thioacetamide, cyanate, diethylurea, tetraethylurea, biuret, alloxan, alloxantine, allantoin, theobromine, ammonium chloride, sodium nitrite, potassium nitrate, urea, glutathione (reduced form), alloxan, L-citrulline, putrescine, L-ornithine, agmatine, L-lysine, L-methionine, L-threonine, L-valine, D-lysine, D-valine, N-acetyl-glycine, L-pyroglutamic acid, histamine, adenosine, deoxyadenosine, cytosine, adenine, thymine, thymidine, uracil, uridine, deoxycytidine, cytidine, guanine, guanosine, xanthine, xanthosine, inosine, DL-α-amino-n-butyic acid, γ-amino-n-butyric acid, ε-amino-n-caproic acid, DL-α-amino-caprylic acid, hippuric acid, parabanic acid, uric acid, urocanic acid, δ-amino-n-valeric acid, 2-amino-valeric acid, gly-glu, ala-gly, ala-his, ala-thr, gly-met, gly-gln, ala-gln, gly-ala, gly-asn, and met-ala.

3. The testing system of claim 1, wherein said phosphorus sources are selected from the group consisting of phosphate, pyrophosphate, trimetaphosphate, tripolyphosphate, hypophosphite, thiophosphate, adenosine 2'-monophosphate, adenosine 3'-monophosphate, adenosine 5'-monophosphate, adenosine 2':3'-cyclic monophosphate, adenosine 3':5'-cyclic monophosphate, dithiophosphate, DL-α-glycero-phosphate, β-glycero-phosphate, phosphatidyl glycerol, phosphoenol pyruvate, phosphocreatine, 2' deoxy glucose 6-phosphate, guanosine 2'-monophosphate, guanosine 3'-monophosphate, guanosine 5'-monophosphate, guanosine 2':3'-cyclic monophosphate, guanosine 3':5'-cyclic monophosphate, glucose 1-phosphate, glucose 6-phosphate, fructose 1-phosphate, fructose 6-phosphate, mannose 1-phosphate, mannose 6-phosphate, arabinose 5-phosphate, cytidine 2'-monophosphate, cytidine 3'-monophosphate, cytidine 5'-monophosphate, cytidine 2':3'-cyclic monophosphate, cytidine 3':5'-cyclic monophosphate, glucosamine 1-phosphate, glucosamine 6-phosphate, phospho-L-arginine, O-phospho-D-serine, O-phospho-L-serine, O-phospho-D-tyrosine, O-phospho-L-tyrosine, uridine 2'-monophosphate, uridine 3'-monophosphate, uridine 5'-monophosphate, uridine 2':3'-cyclic monophosphate, uridine 3':5'-cyclic monophosphate, O-phospho-L-threonine, inositol hexaphosphate, nitrophenyl phosphate, 2-aminoethyl phosphonate, 6-phosphogluconic acid, 2-phosphoglyceric acid, phosphoglycolic acid, phosphonoacetic acid, thymidine 3'-monophosphate, thymidine 5'-monophosphate, methylene diphosphonic acid, and thymidine 3':5'-cyclic monophosphate.

4. The testing system of claim 1, wherein said sulfur sources are selected from the group consisting of sulfate, thiosulfate, tetrathionate, thiophosphate, dithiophosphate, L-cysteine, cysteinyl-glycine, L-cysteic acid, cysteamine, L-cysteine-sulphinic acid, cystathionine, lanthionine, DL-ethionine, glutathione (reduced form), L-methionine, glycyl-DL-methionine, S-methyl-L-cysteine, L-methionine sulfoxide, L-methionine sulfone, taurine, N-acetyl-DL-methionine, N-acetyl cysteine, isethionate, thiourea, thiodiglycol, thioglycolic acid, thiodiglycolic acid, 1-dodecane-sulfonic acid, taurocholic acid, tetramethylene sulfone, hypotaurine, O-acetyl-serine, 3':3' thiodipropionic acid, L-djenkolic acid, and 2-mercaptoethylamine, metabisulfite, dithionite, polysufide, cystine, glycyl-cysteine, L-2-thiohistidine, and S-ethyl-cysteine.

5. The testing system of claim 1, wherein said auxotrophic supplements are selected from the group consisting of L-alanine, L-arginine, L-asparagine, L-aspartic acid, adenine, adenosine, 2'-deoxyadenosine, adenosine 3':5'-cyclic monophosphate, adenosine 3'-monophosphate, adenosine 5'-monophosphate, L-cysteine, L-glutamic acid, L-glutamine, L-glycine, L-histidine, L-isoleucine, guanine, guanosine, 2'-deoxyguanosine, guanosine 3':5'-cyclic monophosphate, guanosine 3'-monophosphate, guanosine 5'-monophosphate, L-leucine, L-lysine, L-methionine, L-phenylalanine, L-proline, L-serine, cytosine, cytidine, 2'-deoxycytidine, cytidine 3':5'-cyclic monophosphate, cytidine 3'-monophosphate, cytidine 5'-monophosphate, L-tryptophan, L-tyrosine, L-threonine, L-valine, D-alanine, D-aspartic acid, thymine, thymidine, thymidine 3':5'-cyclic monophosphate, thymidine 3'-monophosphate, thyrnidine 5'-monophosphate, D-glutarnic acid, (5)4-amino-imidazole-4(5)-carboxamide, DL-α,ε-diaminopimelic acid, D-biotin, DL-α-lipoic acid, caprylic acid, uracil, uridine, 2'-deoxyuridine, uridine 3':5'-cyclic monophosphate, uridine 3'-monophosphate, uridine 5'-monophosphate, p-aminobenzoic acid, shikimic acid, molybdic acid, folic acid, α-keto-isovaleric acid, D-pantothenic acid, hypoxanthine, inosine, 2'-deoxyinosine, inosine 3':5'-cyclic monophosphate, inosine 3'-monophosphate, inosine 5'-monophosphate, thiamine, riboflavin, pyridoxal, pyridoxine, pyridoxamine, quinolinic acid, reduced glutathione, L-homoserine lactone, α-ketobutyric acid, β-nicotinarnide adenine dinucleotide, nicotinic acid, nicotinamide, N-α-acetyl-L-ornithine, L-ornithine, L-citrulline, putrescine, spermidine, spermine, TWEEN® 20, TWEEN® 40, TWEEN® 60, TWEEN® 80, and δ-amino-levulinic acid.

6. The testing system of claim 1, wherein said at least one test substrate is further selected from the group consisting of carbon sources selected from the group consisting of polymers, carbohydrates, acids, esters, amides, amines, alcohols, aldehydes, ketones, amino acids, peptides, and nucleosides.

7. The testing system of claim 6, wherein said carbon sources are selected from the group consisting of dextrin, TWEEN® 40, TWEEN® 60, TWEEN® 80, N-acetyl-D-galactosamine, N-acetyl-D-glucosamine, L-arabinose, D-fructose, L-fucose, D-galactose, α-D-glucose, α-D-lactose, maltose, D-mannitol, D-mannose, D-melibiose, β-methyl-D-glucoside, L-rhamnose, D-sorbitol, D-trehalose, methyl pyruvate, mono-methyl succinate, acetic acid, D-galactonic acid lactone, D-galacturonic acid, D-gluconic acid, D-glucuronic acid, α-ketobutyric acid, D,L-lactic acid, propionic acid, succinic acid, bromosuccinic acid, alaninamide, D-alanine, L-alanine, L-alanyl-glycine, L-asparagine, L-aspartic acid, glycyl-L-aspartic acid, glycyl-L-glutamic acid, D-serine, L-serine, inosine, uridine, thymidine, glycerol, D,L-α-glycerol phosphate, glucose-1-phosphate, and glucose-6-phosphate, α-cyclodextrin, adonitol, D-arabitol, cellobiose, i-erythritol, xylitol, citric acid, D-glucosaminic acid, β-hydroxybutyric acid, γ-hydroxybutyric acid, p-hydroxyphenylacetic acid, itaconic acid, α-ketovaleric acid, malonic acid, quinic acid, sebacic acid, L-histidine, hydroxy L-proline, L-leucine, and D,L-carnitine, glycogen, D-psicose, succinamic acid, glucuronamide, gentiobiose, m-inositol, cis-aconitic acid, L-phenylalanine, L-pyroglutamic acid, phenylethylamine, putrescine, 2-amino ethanol, 2,3-butanediol, lactulose, D-raffinose, formic acid, α-hydroxybutyric acid, L-glutamic acid, L-proline, sucrose, L-ormithine, turanose, α-ketoglutaric acid, D-saccharic acid, L-threonine, γ-aminobutyric acid and urocanic acid.

8. The testing system of claim 1, wherein said testing device comprises more than 95 testing wells.

9. The testing system of claim 1, wherein said testing wells further contain a gel-initiating agent and said gelling agent in said inoculating fluid remains ungelled until said at least one cell type is placed in said testing wells.

10. The testing system of claim 1, further comprising at least one antimicrobial.

11. The testing system of claim 10, wherein said at least one antimicrobial is present in said testing wells.

12. The testing system of claim 10, wherein said inoculating fluid further comprises said at least one antimicrobial.

13. The testing system of claim 1, further comprising at least one colorimetric indicator.

14. The testing system of claim 13, wherein said at least one calorimetric indicator is present in said testing wells.

15. The testing system of claim 13, wherein said inoculating fluid further comprises said at least one colorimetric indicator.

16. The testing system of claim 13, wherein said colorimetric indicator is selected from the group consisting of chromogenic compounds, fluorochromic compounds, fluorogenic compounds, pH indicators, oxidation-reduction indicators, and luminogenic compounds.

17. The testing system of claim 16, wherein said oxidation-reduction indicator comprises a tetrazolium dye.

18. The testing system of claim 16, wherein said oxidation-reduction indicator comprises redox purple.

19. The testing system of claim 1, wherein said inoculating fluid further comprises at least one additional substrate selected form the group consisting of carbon sources, nitrogen sources, phosphorus sources, sulfur sources, and auxotrophic supplements.

20. The testing system of claim 1, wherein said inoculating fluid further comprises microorganisms selected from the group consisting of bacteria and fungi.

21. The testing system of claim 1, further comprising a detection means, wherein said detecting is visual.

22. The testing system of claim 21, wherein said detecting is performed by an instrument.

23. The testing system of claim 22, wherein said instrument comprises a video camera.

24. The testing system of claim 21, wherein said detecting is conducted over time.

* * * * *

UNITED STATES PATENT AND TRADEMARK OFFICE
CERTIFICATE OF CORRECTION

PATENT NO.   : 6,472,201 B1                                                             Page 1 of 1
DATED        : October 29, 2002
INVENTOR(S)  : Barry Bochner et al.

It is certified that error appears in the above-identified patent and that said Letters Patent is hereby corrected as shown below:

Column 58,
Line 26, please delete "calorimetric" and insert -- colorimetric --.

Signed and Sealed this

Eleventh Day of March, 2003

JAMES E. ROGAN
*Director of the United States Patent and Trademark Office*